United States Patent
Nasab et al.

(10) Patent No.: US 7,252,664 B2
(45) Date of Patent: Aug. 7, 2007

(54) SYSTEM AND METHOD FOR MULTI-CHANNEL RF ENERGY DELIVERY WITH COAGULUM REDUCTION

(75) Inventors: Michael Nasab, Boulder Creek, CA (US); Eric K. Y. Chan, San Carlos, CA (US)

(73) Assignee: Cardima, Inc., Freemont, CA (US)

( * ) Notice: Subject to any disclaimer, the term of this patent is extended or adjusted under 35 U.S.C. 154(b) by 469 days.

(21) Appl. No.: 10/846,260

(22) Filed: May 14, 2004

(65) Prior Publication Data
US 2005/0010206 A1 Jan. 13, 2005

Related U.S. Application Data

(63) Continuation-in-part of application No. 10/333,113, filed on Jan. 14, 2003, now Pat. No. 6,936,047.

(60) Provisional application No. 60/203,847, filed on May 12, 2000.

(51) Int. Cl.
*A61B 18/18* (2006.01)
(52) U.S. Cl. ...................................... 606/34
(58) Field of Classification Search .......... 606/1, 606/32–42, 48–50
See application file for complete search history.

(56) References Cited

U.S. PATENT DOCUMENTS

| | | | |
|---|---|---|---|
| 5,318,563 A | 6/1994 | Malis et al. | |
| 5,540,681 A * | 7/1996 | Strul et al. | 606/34 |
| 5,759,847 A | 6/1998 | Panescu et al. | |
| 5,800,432 A | 9/1998 | Swanson | |
| 5,810,802 A | 9/1998 | Panescu et al. | |
| 5,871,481 A * | 2/1999 | Kannenberg et al. | 606/34 |
| 5,997,528 A * | 12/1999 | Bisch et al. | 606/1 |
| 6,123,702 A | 9/2000 | Swanson et al. | |
| 6,183,468 B1 | 2/2001 | Swanson et al. | |
| 6,245,065 B1 | 6/2001 | Panescu et al. | |
| 6,409,722 B1 * | 6/2002 | Hoey et al. | 606/34 |
| 6,796,980 B2 * | 9/2004 | Hall | 606/34 |
| 2004/0006337 A1 | 1/2004 | Nasab et al. | |

FOREIGN PATENT DOCUMENTS

WO  WO 00/15130  3/2000

* cited by examiner

*Primary Examiner*—Michael Peffley
(74) *Attorney, Agent, or Firm*—Fitch, Even, Tabin & Flannery

(57) ABSTRACT

A system and method for efficient delivery of radio frequency (RF) energy includes a backplane. At least a single channel card is removably coupled to the backplane for controlling the amount of RF power delivered through a single channel via an electrical coupling to at least one ablation electrode or a catheter. The at least one channel card provides a gradual increase in RF power calculated in real-time during an initial ramp-up phase, and to limit the delivery of RF power through the electrical coupling based on a received temperature of cardiac tissue in contact with the at least one ablation electrode, thereby reducing the likelihood coagulum formation.

27 Claims, 19 Drawing Sheets

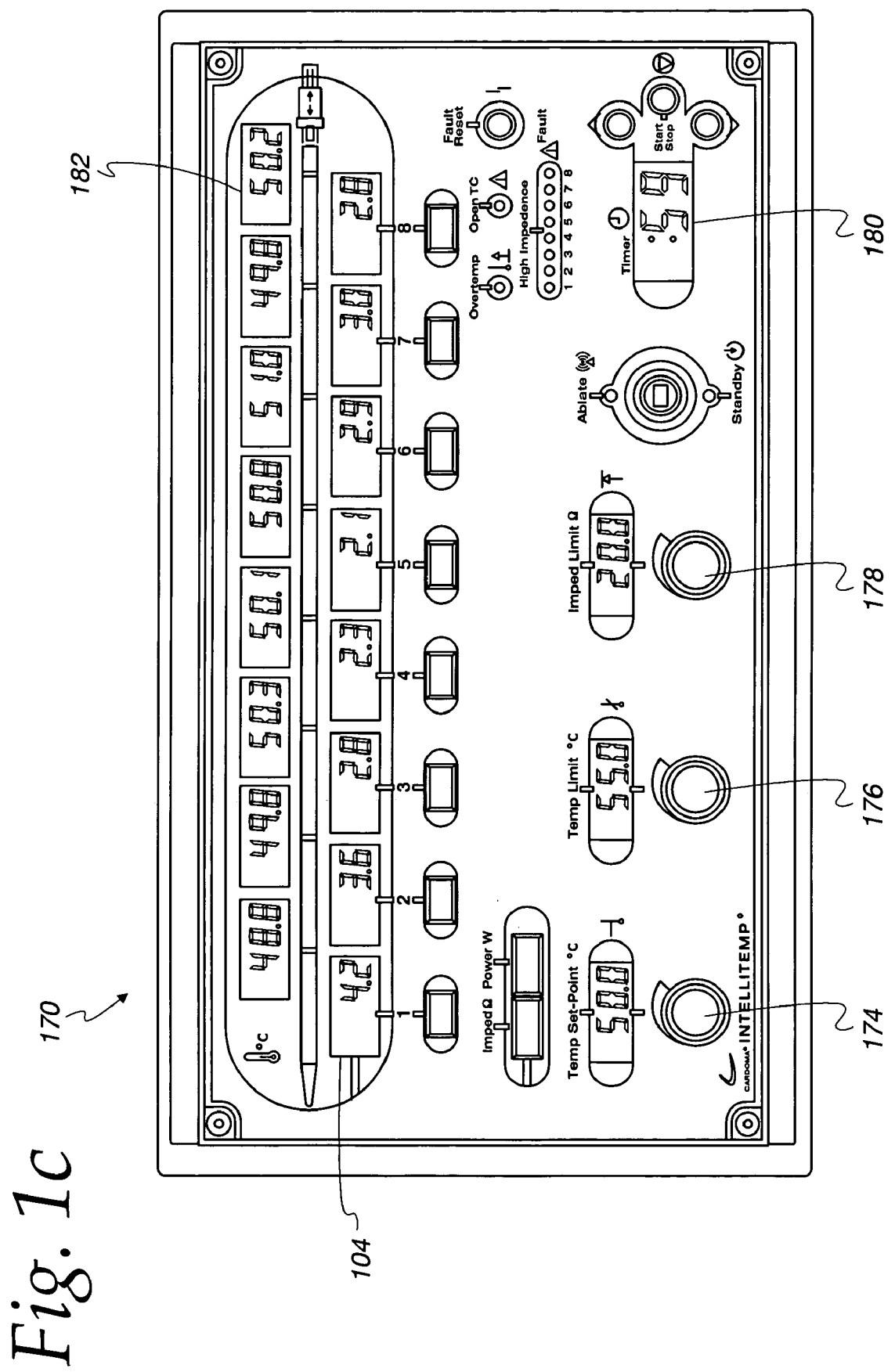

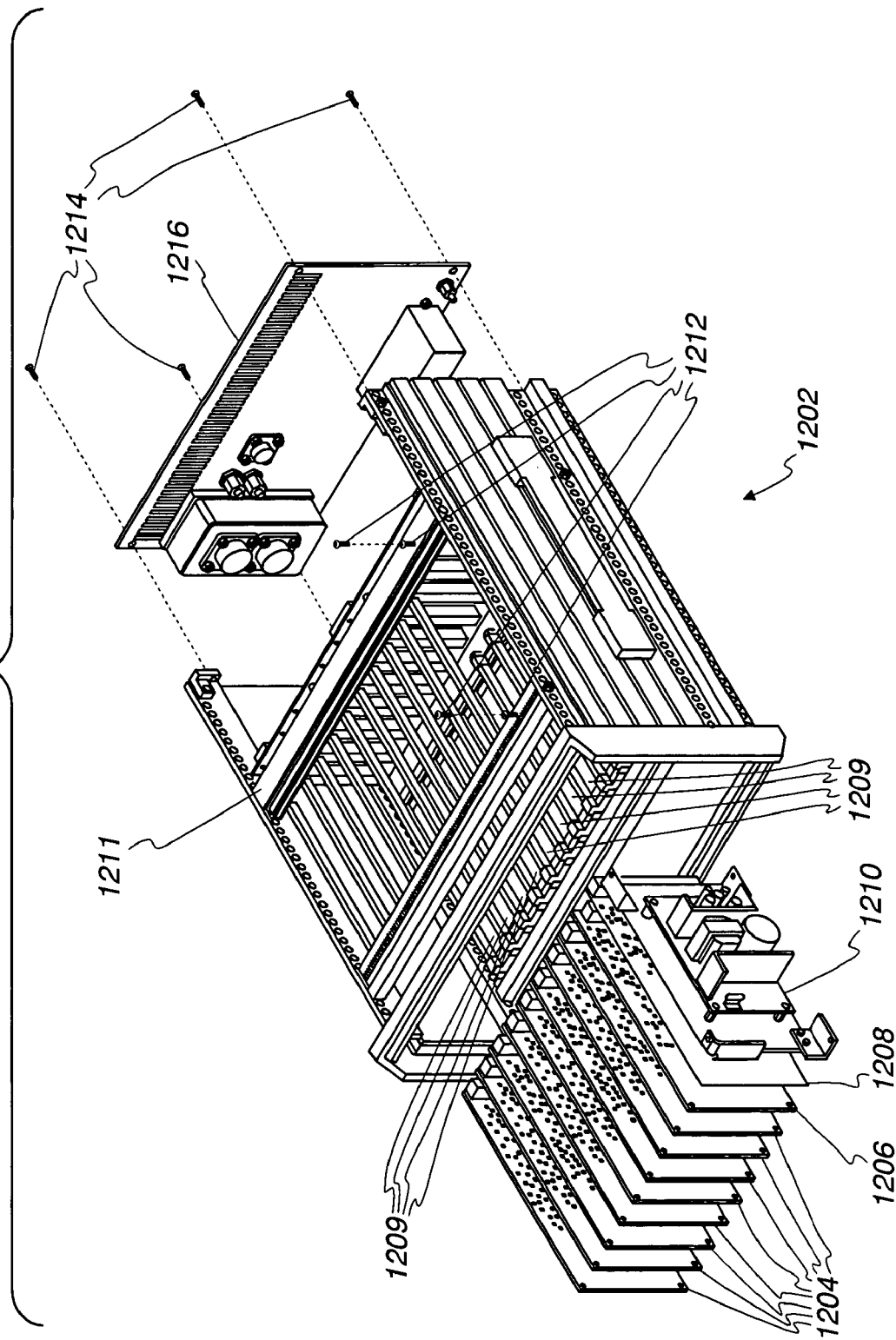

SYSTEM AND METHOD FOR MULTI-CHANNEL RF ENERGY DELIVERY WITH COAGULUM REDUCTION

CROSS-REFERENCE TO RELATED APPLICATIONS

This application is a continuation-in-part of U.S. application Ser. No. 10/333,113 filed on Jan. 14, 2003, now issued as U.S. Pat. No. 6,936,047 and incorporated herein by reference in its entirety, which claims priority from U.S. Provisional Application No. 60/203,847, filed May 12, 2000 and also incorporated herein by reference in its entirety.

FIELD OF THE INVENTION

The field of the invention relates to methods and devices for energy delivery to a catheter or probe. More specifically, the invention relates to a modular and decentralized control system to deliver energy to an ablation catheter surgical probe.

BACKGROUND OF THE INVENTION

Radio frequency energy may be used to treat certain cardiac abnormalities, such as fibrillation, by ablating cardiac tissue. Radio frequency energy is delivered by RF generators in two phases: (i) the "ramp up" phase in which a relatively high amount of power is delivered to an ablating electrode until a desired set temperature is sensed by a thermocouple or thermistor, and (ii) the "regulation" phase in which power is still being delivered but regulated at a lower level to maintain the desired set temperature. This target temperature is predetermined by the operator, and is generally 50° to 55° C. for ablation of cardiac tissue.

Most RF generators have software modules which run simultaneously on portable computers during RF energy delivery to log the ablation episode. Typically, the parameters logged are sensed impedance, power delivered, as well as tissue temperature sensed by either thermistors or thermocouples. This information is typically used for post-procedural review.

One objective in RF ablation of cardiac tissue is to create deep lesions in the cardiac tissue while avoiding coagulum formation. RF energy must be delivered efficiently into the tissue, and not delivered and lost into the blood medium. Previous methods and systems are not adequate to assure that RF energy is delivered efficiently to cardiac tissue during an ablation procedure.

In previous systems, a master control card with a master controller is typically used to control the operation of various system components. Since the control is centralized, the loss of controller card means the system becomes inoperable.

SUMMARY OF THE INVENTION

The system and method of the present invention deliver RF energy to cardiac tissue simultaneously through a series of channels to a catheter. The delivery is made in a manner that minimizes the risk of an ineffective ablation procedure due to coagulum formation.

In many of these approaches, a plurality of channel cards are interconnected via a backplane. The channel cards are coupled to a catheter and supply RF energy to the catheter. Each channel card supplies energy to one channel of the catheter. The channel cards may include analog or other types of circuitry organized into modules to control the amount of energy delivered to the catheter.

In many of these embodiments, an information processor and RF output controller are located on the channel cards to carefully control the rate and amount of RF energy delivered from an RF generator to the cardiac tissue being ablated to improve the effectiveness of an ablation procedure. The information processor and RF output controller assure that RF energy is increased gradually during the initial ramp-up phase. Furthermore, the information processor and RF output controller regulate delivery of RF energy during the ablation episode using information gathered from a series of sensors that are delivered to the site of ablation, preferably as part of an ablation catheter. The series of sensors include a series of temperature sensors and/or a multiplicity of current sensors. This feedback-control assures that proper temperature is maintained at the site of ablation and provides the ability to abort an ablation procedure if effective tissue contact is not established or maintained throughout the ablation procedure.

The system and method of the present invention also provides modular channel cards to deliver RF energy to the catheter. The system is substantially analog-based and does not include a central controller. However, in another approach, the system may be based upon other technology, for instance, digital components or neural networks. Channel cards can be easily and quickly replaced and mounted by a user and the number of channels can be easily configured to suit the specific requirements for a particular field of use.

BRIEF DESCRIPTION OF THE DRAWINGS

FIGS. 1A-1C are schematic diagrams of certain embodiments of the information processor and RF output controller and system of the current invention (FIG. 1A), and user interfaces (FIGS. 1B and 1C) for the information processor and RF output controller.

FIG. 10A shows results from a patient study when gradual power delivery was not applied and maximum power was set at 50 W. FIG. 10B shows results from a patient study using systems and methods according to the current invention where gradual power delivery was applied for each ablation episode and maximum power of the RF generator was set at 30 W;

FIGS. 12a-f are mechanical perspective views of a system for delivering RF energy to a catheter according to the present invention.

DETAILED DESCRIPTION OF THE PREFERRED EMBODIMENTS

The methods and systems of the current invention utilize a novel information processor and RF output controller 100, also called a multi-channel RF ablation interface herein, to regulate delivery of radio frequency (RF) energy from an RF generator 150, also called an RF energy source herein, to cardiac tissue via an electrical coupling connected to a series of ablation electrodes of an ablation device, which may be a catheter or therapeutic probe. The information processor and RF output controller assure that energy is delivered in a gradually increasing manner during an initial ramp-up phase to an ablation temperature set point, and at a rate thereafter that is feedback-regulated to maintain the set-point temperature of the cardiac tissue at the site of ablation. Preferably, the temperature set point is selectable by a user. The delivery of energy is also preferably feedback-regulated by other parameters such as impedance, current, and/or power delivered to the ablation catheter to assure that effective contact between the ablation electrode and the cardiac tissue is maintained. Although the systems and methods are described herein with relation to ablating cardiac tissue, it will be understood that they are not limited to ablating cardiac tissue only but may be applied to any surgical or therapeutic area involving any area of the human body. Furthermore, although the systems and methods are described in relation to an ablation catheter, it will be understood that any type of therapeutic probe may be used.

The components of the present invention may be located on a plurality of channel cards coupled to a backplane. Each of the channel cards delivers RF energy to a single channel of the catheter. The channel cards are easy to replace and an optimum number may be installed on a backplane depending upon the requirements of the system. The channel cards themselves are organized into discrete modules, which can be easily replaced or modified. For instance, one of the modules may be an analog computer. Another example of a module is a pulse width modulator (PWM).

The modules comprising the information processor and RF output controller may be substantially analog-based and capable of delivering energy to each electrode of the series of ablation electrodes independently. In other approaches, the components may be based upon other technologies, such as digital circuitry. In certain preferred embodiments, described herein, the information processor and RF output controller use analog methods for information processing and pulse with modulation for RF energy control.

In preferred embodiments, the information processor and RF output controller are capable of delivering RF energy to the electrodes of the series of electrodes in any order or combination using methods described herein. Preferably, a user can select the electrode, or combination of electrodes, to which the information processor and RF output controller will deliver energy.

Figure 1A:
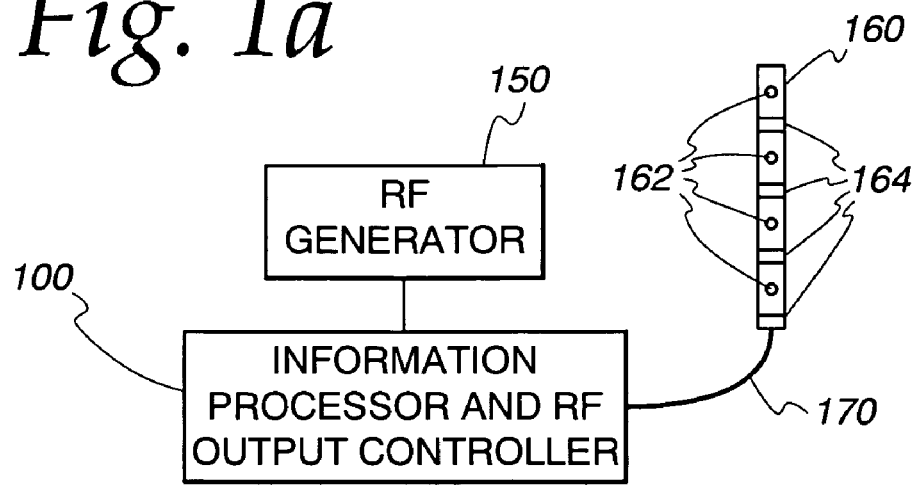

As shown in FIG. 1A, the described information processor and RF output controller 100, also referred to herein as a multi-channel RF ablation interface, is intended to make cardiac lesions in the human heart in conjunction with commercially available radio-frequency (RF) lesion generator 150 and ablation catheter 160, such as manufactured by Cardima. The interface regulates RF energy delivery from the RF generator 150 to the ablation catheter 160 by temperature feedback using readings of thermocouple sensors 162 embedded in the catheter 160, as well as by other parameters such as impedance and differential impedance. Electrical communication between the information processor and RF output controller and the catheter occurs via an electrical coupling 170. The feedback regulation functions to maintain the electrode temperature near the preset temperature value, and to assure that effective contact between ablation electrodes 164 and cardiac tissue has been maintained for effective transmission of energy from the electrodes 164 to the cardiac tissue. In addition, a catheter or catheters may be used in a bi-polar mode in contrast to the mono-polar catheters described herein.

The general design features of the multi-channel RF ablation interface (i.e. the information processor and RF output controller) of the current invention include an operating RF frequency range of about 350 to about 550 kHz; multiple, preferably eight (8), regulated electrode channels; maximum power RF energy input of about 100 watts; maximum power RF energy output for each channel of 30 Watts; and a function that provides gradually increasing power delivery at start-up. As described below, preferably the power for each channel is typically set at about 25 to 35 watts, most preferably about 30 watts. The information processor and RF output controller are typically capable of receiving real-time temperature monitoring information from sensors 162 on the ablation catheter 160, and compare this information with a user defined set temperature. This temperature information is used to control the titration of RF energy to reach and maintain the set temperature, or to shut off RF energy delivery if a certain over-temperature cutoff is reached. The information processor and RF output controller also calculate real-time impedance and output power based on measurements sensed from the circuitry, then compare this calculated information to user set limits, wherein if a limit is exceeded, delivery of energy is terminated. Preferably, the information processor and RF output controller 100 are capable of receiving and processing this information for each output channel of the circuitry. The information processor and RF output controller may use analog or digital methods for receiving and processing monitoring information from the sensors. In a preferred embodiment, real-time analog data acquisition and computation methods are used.

The information processor and RF output controller and/or the RF source have the ability to deliver RF energy in a gradual manner when energy delivery is initiated. That is, either in a manual, or preferably an automated manner, upon initiation of delivery of RF energy to an ablation electrode, power is initiated at a level that is below the maximum power level used to attain a temperature set point for the cardiac tissue being ablated. Power is then gradually increased over a duration of about 8 to 15 seconds, preferably 10 seconds, typically until it reaches the maximum power. For example, but not intended to be limiting, when using the Radionics RFG-3E generator in the manual mode, power may be commenced with a setting of 10 watts, and then gradually increased within 10 seconds by adjusting the power knob on the RF generator to reach a set temperature of 50° C. for endocardial ablation, and up to 80° C. for surgical applications while not overshooting a maximum of 30 watts, all the while maintaining total RF delivery time at 60 to 120 seconds. Rather than a manually controlled mode, in a preferred approach, the processor and RF output controller and RF output controller of the current invention, as described below in more detail, gradually increase power automatically upon initiation of RF energy delivery.

Figure 1B:
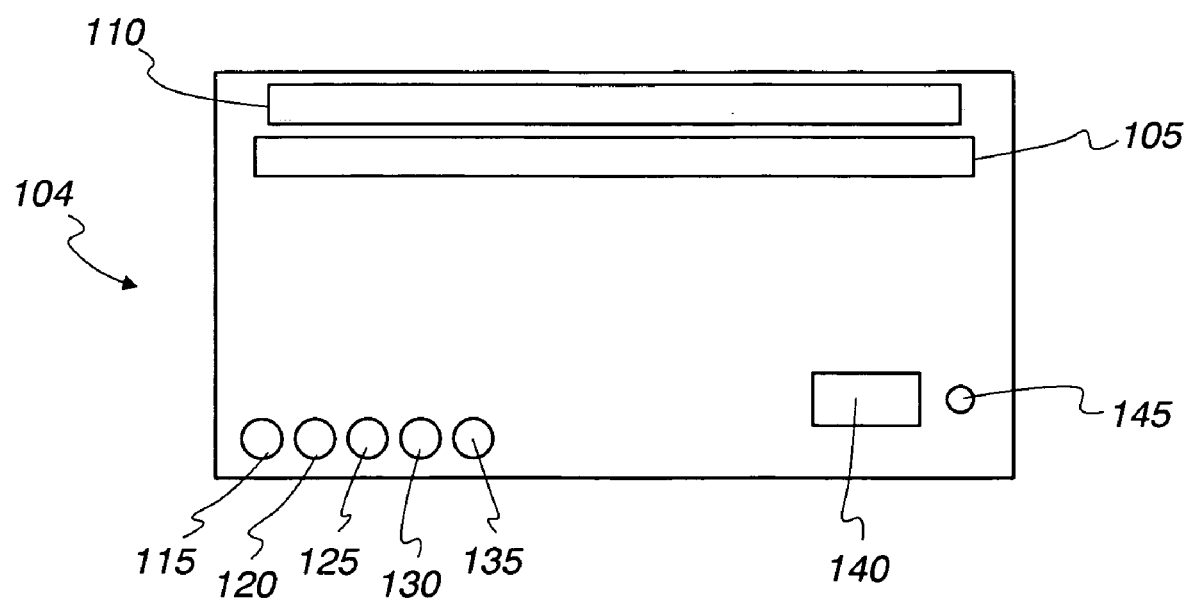

As shown in FIG. 1B, the information processor and multichannel simultaneous RF output controller include a user interface 104 containing displays 105 and 110, and adjustment knobs 115, 120, 125, 130, 135 to facilitate monitoring and control of the parameters described above. For example, the display 105 may show parameter values, and the display 110 may be a separate thermocouple digital display.

The user interface 104 (information processor and RF output controller interface) typically contains a series of adjustment knobs 115, 120, 125, 130, 135 to facilitate setting values for the parameters described above. For example, the information processor and RF output controller interface 104 typically includes an ablation temperature set point control 115 and over-temperature set point control 120. Typically the ablation temperature set point control 115 has a range of from about 50° C. to about 80° C., and the over-temperature set point control 120 has a range from about 55° C. to about 85° C. Additionally, the information processor and RF output controller preferably can determine impedance and differential impedance, typically measures power output and includes a power limit adjustment knob 125. Preferably, the information processor and RF output controller interface 104 has an impedance limit control 130 which typically can be set in the range from about 50 to about 1000 Ohms. Additionally, the information processor and RF output controller interface 104 preferably has a differential impedance set point control 135 from 10 to 300 Ohms.

Another example of a user interface 170 is shown in FIG. 1C and is suited for electrophysiology applications. The interface 104 includes a temperature set point knob 150, temperature limit knob 176, impedance limit knob 178, timer 180, and displays 180 and 182. The interface 170 does not include a delta-impedance knob. The functions of the knobs have been described above. The display 184 may show parameter values, and the display 182 may be a separate temperature display for temperature values of the thermocouples.

Returning to FIG. 1B, the information processor and RF output controller user interface 104 may contain a fault status indicator 140 which may project any type of signal detectable by a user if the information processor and RF output controller detect a parameter value that exceeds a preset limit. For example, the fault status indicator may be triggered if the temperature of the cardiac tissue exceeds a maximum temperature set by the user. The fault status indicator may project a visual or auditory signal. In certain preferred embodiments, the user interface includes a reset switch which resets the fault status indicator.

The user interface 104 on the information processor and RF output controller may have one or more of the following additional features, as described in more detail in the specific embodiment disclosed below:
1. an ablate/pace mode select switch to switch between ablation and electrocardiogram recording modes;
2. ablate, RF active and pace indicator LEDs;
3. a bipolar pacing stimulator selector switch;
4. a parameter display pushbutton switch;
5. an illuminated on/off electrodes select switch; and
6. a real-time parameter data collection for post processing and data analysis in commercial software programs such as, but not limited to, LabView and Excel formats.

As mentioned above, the information processor and RF output controller of the current invention regulates delivery of RF energy from an RF energy source through multiple channels simultaneously to cardiac tissue. The primary functional building block of all radio frequency (RF) energy sources developed for tissue ablation is an electronic circuit called an oscillator which generates sinusoidal waveforms at particular operating frequencies. This waveform is consequently amplified to deliver the required wattage required for tissue ablation. The operating frequency of this RF oscillator typically is within the range of 350 to 550 kHz. The quality of the oscillator and ancillary electronics design impinges on the stability of the resulting operating frequency. Hence, this operating frequency may "drift" slightly if the oscillator design is unstable. Typically, this frequency jitter has imperceptible influence on the resulting tissue lesion. However, certain RF oscillators or associated electronics systems generate and deliver a skewed or distorted sine wave signal that has spurious noise spikes and/or harmonics riding on top of it. Such "noisy" and skewed RF waveforms may result in undesirable noise artifacts may have the potential of promoting coagulum formation if they are present during the ablation process. Therefore, it is desirable for the current invention to use an RF source which produces a relatively pure and stable sine wave, preferably as pure and stable a sine wave as possible.

As described above, the information processor and RF output controller 100 are connected to and regulate RF energy delivered to multiple electrodes arranged in various configurations at the distal end of a catheter. In catheter ablation, electrodes of the catheter deliver the RF current into biological tissue. This RF energy in turn heats the tissue by causing ionic friction within the tissue and fluid medium encompassed by the electric field. When monitored, this temperature rise caused by the conversion of electrical to thermal energy can be used as a guide in RF catheter ablation. Its measurement is facilitated by the placement of thermal sensors, either thermocouples or thermistors, underneath or juxtaposed with the ablative electrodes. Not only can the sensed temperature be used to ascertain the quality of electrode-tissue contact and predict lesion size, it can also be utilized by the RF generator as a feedback signal to automatically regulate the output power to arrive at or maintain a temperature set-point predetermined by the end-user.

Many ablation catheters are known in the art and can be used with the systems and methods of the current invention. Typically, catheters for use with the current invention have multiple electrodes and thermal sensors in close proximity to these electrodes, as discussed above. Furthermore, preferred catheters allow relatively higher electrode current densities which allow lower maximum RF generator power settings, such that effective ablation can be performed at 35 W, and more preferably 30 W, rather than 50 W.

Figure 2A:
FIGS. 2A-C show catheter arrangements for efficient ablation according to the present invention.
Figure 2B:
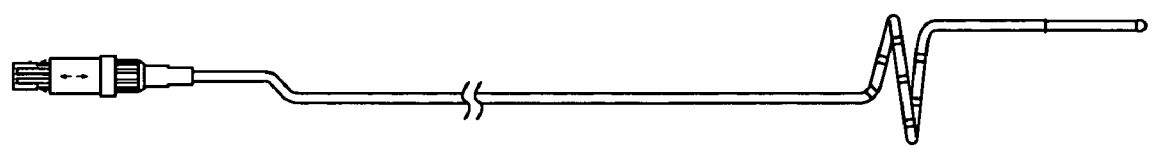
Figure 2C:
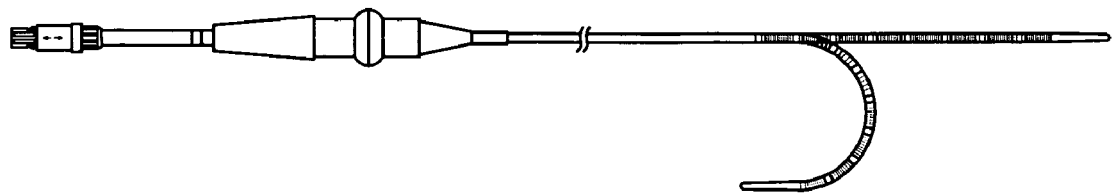

An example of a preferred catheter (i.e., the CARDIMA REVELATION® TX 3.7 Fr catheter) for use in the current invention is illustrated in FIGS. 2A-2C. The catheter was developed for right atrial linear MAZE ablation, and has eight electrodes with thermocouples located in between the electrodes, to accurately sense localized tissue temperature at the ablation site. This preferred catheter has eight 6 mm coil electrodes with 2 mm inter-electrode spacing, and 8 thermocouples located proximal to each electrode in the inter-electrode spaces. A 9 Fr steerable guiding catheter called the NAVIPORT® may be used in conjunction with this catheter to aid in placement. Experience with the 3.7 Fr REVELATION Tx microcatheter has shown that it is successful in creating transmural lesions narrower and with smaller surface area than those created by standard 8 Fr ablation catheters.

In order to switch between each of the multiple electrodes and their corresponding thermocouples or thermistors, manual switchboxes interfacing multi-electrode catheters to single-channel RF generators, as well as automatic sequencing multi-channel RF energy generators have been developed and are now available in the marketplace. These switchboxes and multi-channel RF generators deliver RF energy to these electrodes in a consecutive, sequential fashion. In addition, there are also newer, higher power (e.g., 150 W) RF generators which deliver RF energy simultaneously to multiple electrodes. These latter systems differ in design by how RF energy is "split" among the various electrode channels. This present invention presents a multichannel F ablation system which uses pulse width modulation to govern the amount of RF energy being delivered at each channel, incorporating temperature feedback information per channel as well as from neighboring channels.

Figure 3:
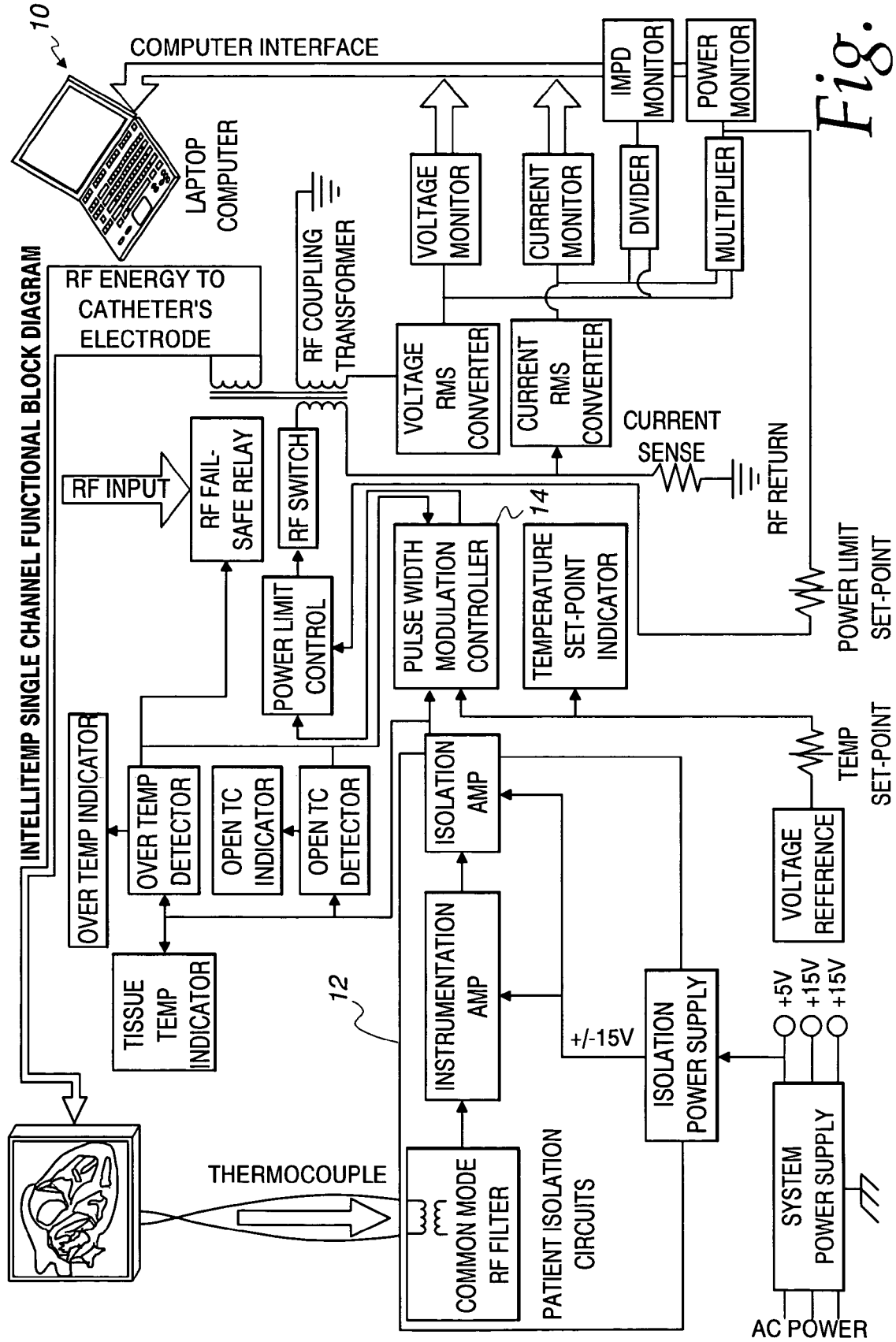
FIGS. 3, 4a and 4b show schematic block diagrams of a modular information processor and RF output controller in accordance with the invention, for regulating delivery of RF energy to cardiac tissue through an ablation catheter according to the present invention.
Figure 4A:
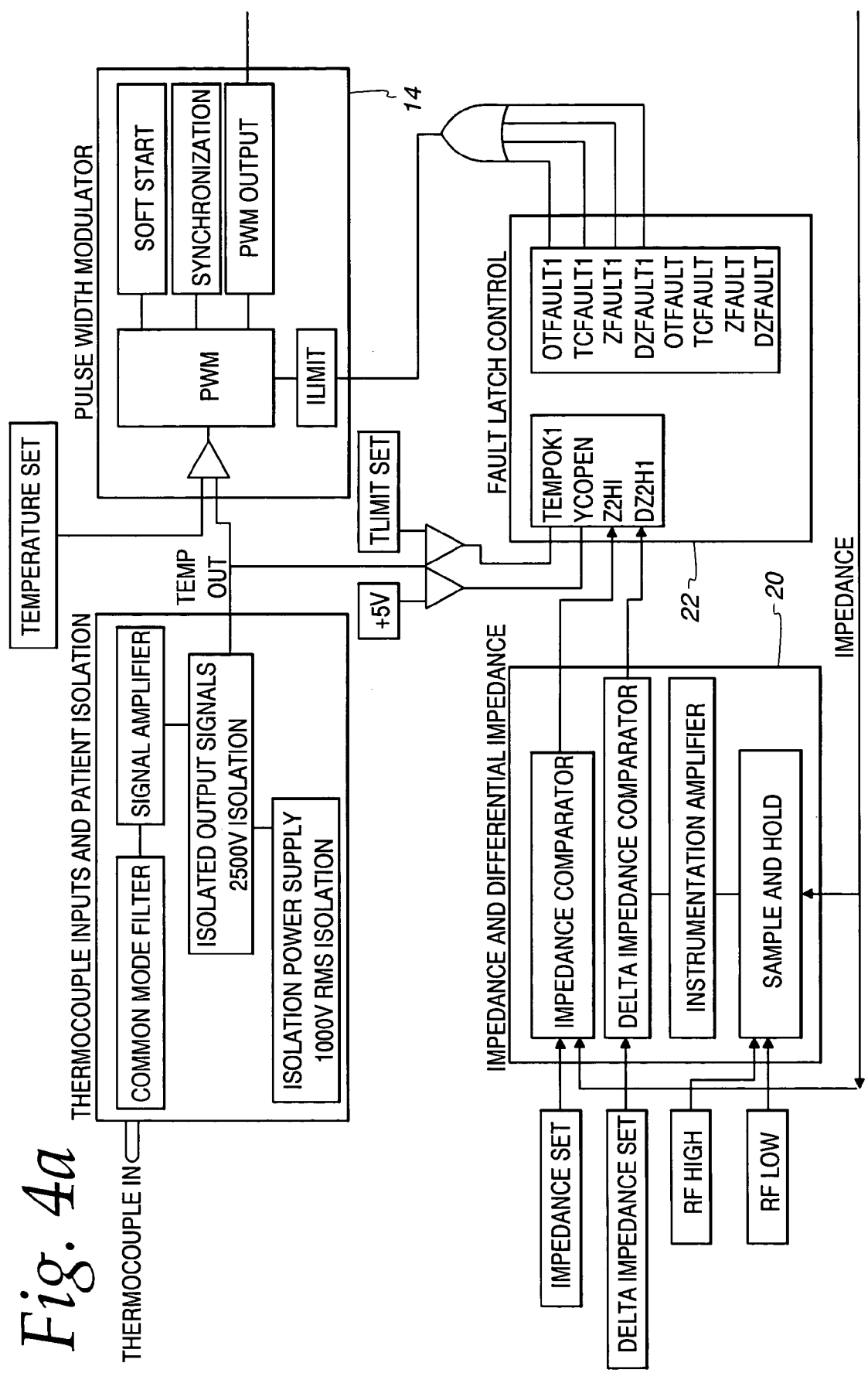
Figure 4B:
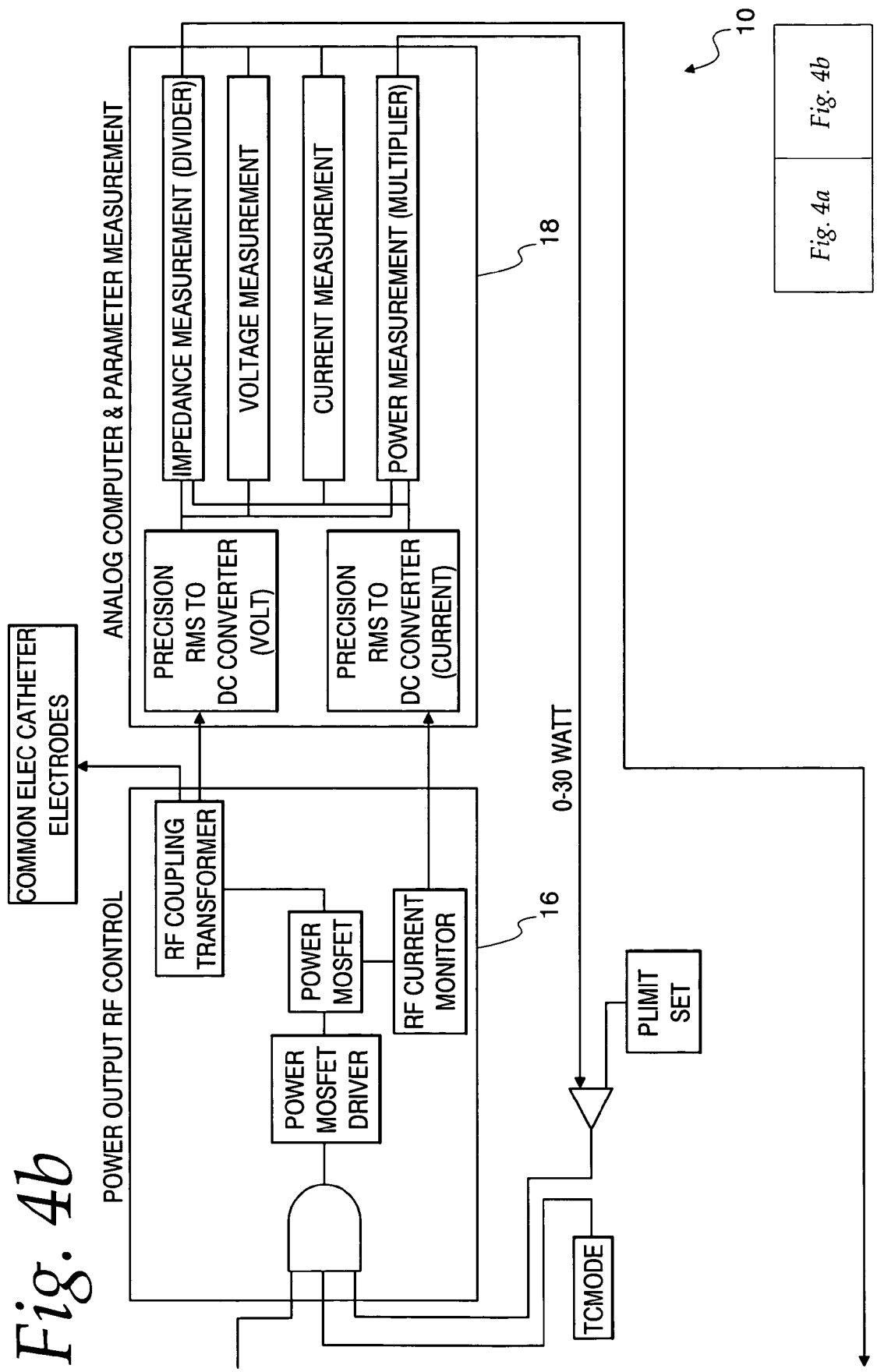

With these general features of a system for the delivery of RF energy to cardiac tissue according to the present invention, a specific embodiment is diagrammatically illustrated in FIGS. 3 and 4. The described embodiment provides a specific multi-channel RF ablation system with the general features illustrated in FIGS. 1A and 1B. The multichannel information processor and RF energy controller 100 provide up to eight channels (switch selectable) of precise RF energy to the catheter's electrodes as well as displays the tissue temperature and impedance in real time. Measurement of the RF power delivered to the tissue, RF current, and RF voltage, as well as the differential impedance for each of the ablation elements, is also provided. All signals are available for computer monitoring or optionally displayed via front panel digital meters. The system incorporates a medical grade power supply approved by the international safety agencies. This power supply can be used for various line voltages and frequencies without any modification. The system is designed to handle up to 100 watts of input power RF energy. Utilizing an analog computer unit (ACU), the system continuously monitors and adjusts the precise RF energy delivered to each electrode.

The following are features of the pulse width modulation implementation for the system: (1) soft start power-on operation; (2) compensation for the lag in thermocouple response time; and (3) PWM synchronization for all eight channels.

Over-temperature detection is provided for each channel of the system. RF energy is latched off for the entire system if an over-temperature condition is detected. Operation is resumed by power cycling or pushbutton reset. Open thermocouple detection inhibits operation of only the faulty channel. Operation is resumed automatically when the fault is cleared. The system is designed to comply with the requirements and standards of international electrical safety codes. It utilizes isolated circuits for all patient connections to insure patient safety even with failed components. This applies to both the thermocouple amplifiers, and the RF output circuitry. The over-temperature cutoff limit is provided to cut off all power delivered to the catheter in the event that any thermocouple reaches a preset over-temperature limit. Adjustment range for this function is from 55° C. to 90° C.

A front panel control and display unit is provided which allows a user to set a number of parameters. For example, the front panel control and display can be used to set the maximum power value sent to any one electrode (Adjustment range: 1-30 watts). The impedance cutoff circuitry monitors each channel individually and will cause the power delivery to be interrupted from a given electrode when that electrode's impedance rises above a preset limit. The front panel control and display (one for the entire unit) provide a control button or knob for setting the impedance cutoff limit (Adjustment range: 50-1000 Ohms). The differential impedance cutoff circuitry monitors each channel individually and will interrupt power delivered to a given electrode if that electrode's impedance rises by a preset differential (above the lowest value during a given ablation run). The front panel control and display provides a knob for setting the differential impedance cutoff limit (Adjustment range: 10-300 Ohms). In order to prevent an RF generator trip-out due to low impedance (as can occur when several electrodes are running in parallel simultaneously), an active impedance network (dummy loads) are placed between the RF generator and the ablation circuitry.

A mode switch (ablate/pace) is provided for switching between ablation and electro-cardiogram recording modes, as well as pace threshold determination mode. Appropriate filtering is designed to allow recording of electrocardiogram during ablation or pacing modes. Modes of Operation:

(Mode 1) Used for catheters that utilize thermocouples between electrodes (e.g., thermocouple 1 is proximal to thermocouple 2). The system will monitor temperature on both sides of each electrode and regulate the temperature based upon the higher temperature, except for the most distal electrode, which has only one nearest thermocouple.

Mode 2) Used for catheters utilizing thermocouples either under or soldered directly onto each electrode.

The channel card functional block diagram (FIGS. 3 and 4) of the system 10 provide thermocouple inputs and patient isolation 12, pulse width modulator 14, power output RF control 16, analog computer and parameter measurement 18, impedance and differential impedance 20, fault latch control 22, and fault status 28. In this example, the components are substantially analog and modular in nature. That is, the components are a series of separate modules that are placed on the channel card. However, the modules may include or may be primarily based upon other technologies such as digital circuitry.

The common mode input filter is designed to handle high common mode of RF energy level on the thermocouples. The isolation circuits, both the power supply and the thermocouple amplifiers, are designed to isolate the patient from the main power source circuitry by 2500 volts.

The pulse width modulator (PWM) 14 regulates the RF energy by comparing the delivered RF power (computed by the analog computer) to the preset value (PLIMIT). It also provides soft start for each channel card as well as synchronization circuitry for all eight channels. The soft start is a safety feature active at power on that gradually ramps up the voltage to prevent spikes on the electrodes.

Figure 5A:
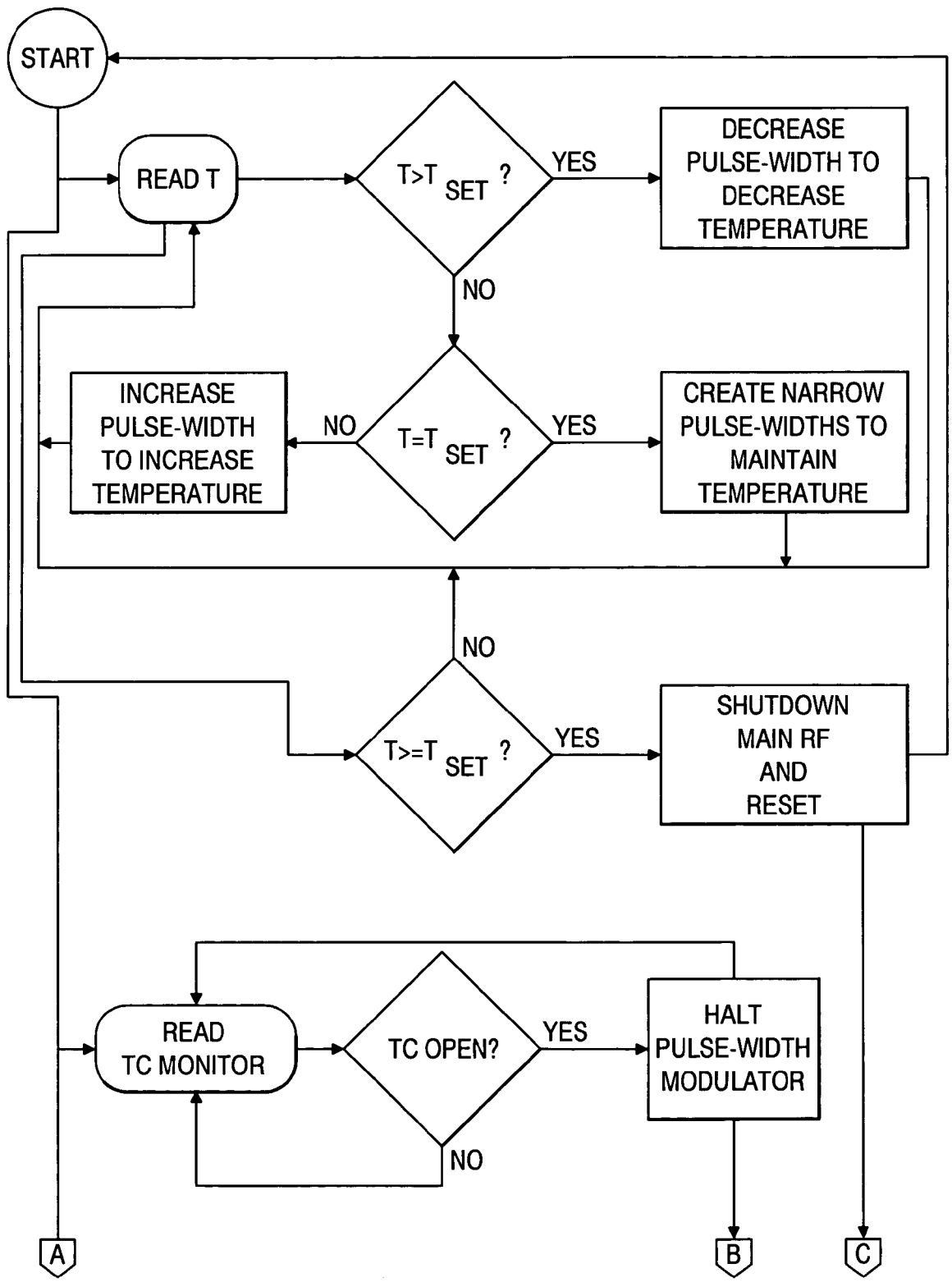
FIGS. 5A and 5B provide flow diagrams for the temperature measurements according to the present invention.
Figure 5B:
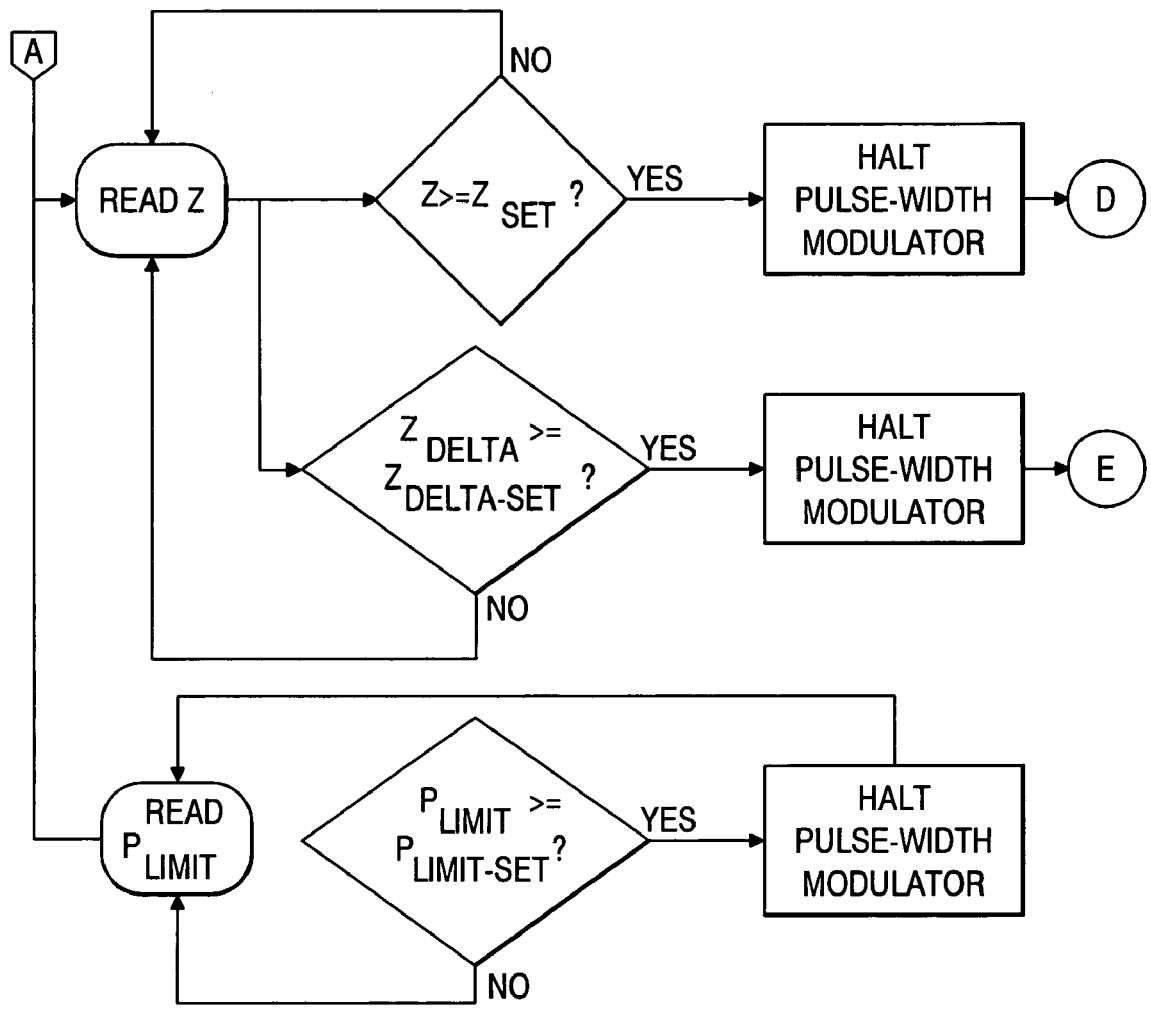
Figure 5B:
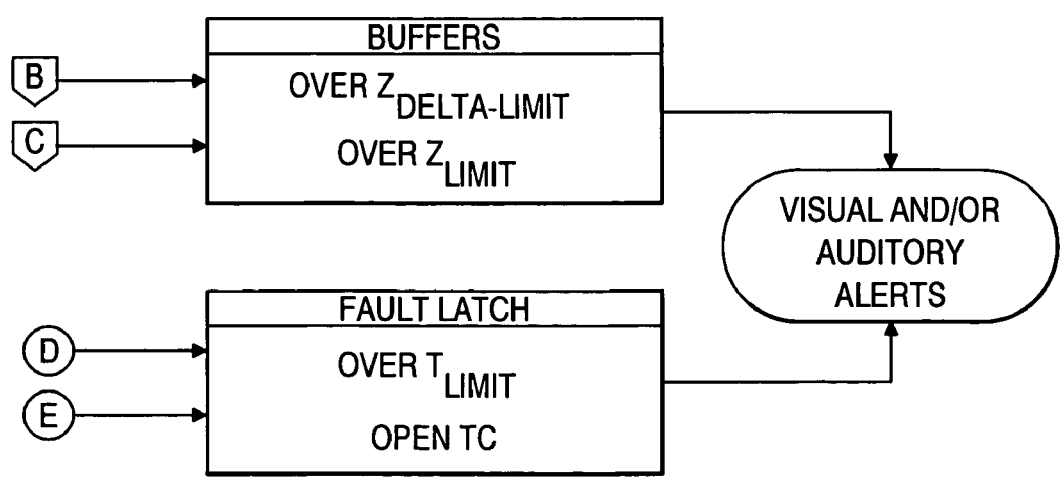

As shown diagrammatically in FIGS. 5A-B, the amount of energy delivered to the RF coupling transformer is directly proportional to the pulse width generated by the PWM circuitry based on the temperature feed back from the catheter's thermocouple. In the preferred example of an ablation catheter for the current invention described above, each channel has a corresponding thermocouple (T/C) sensor which provides temperature feedback information at the tissue site immediately proximal to the electrode delivering RF energy. The RF output for each electrode is modulated by a PWM chip on the channel card. The commercially available PWM device used is the Unitrode High Speed PWM Controller UC3823, or the equivalent chip made by Micro-Linear, ML4823. Temperature input signals sensed from neighboring T/C's are used to control the pulse-width modulator (PWM) outputs. The lower the input voltage corresponding to an input temperature, the longer the "on time" duration. Conversely, the higher the input voltage corresponding to a sensed input temperature, the shorter the "on time" duration.

Figure 6:
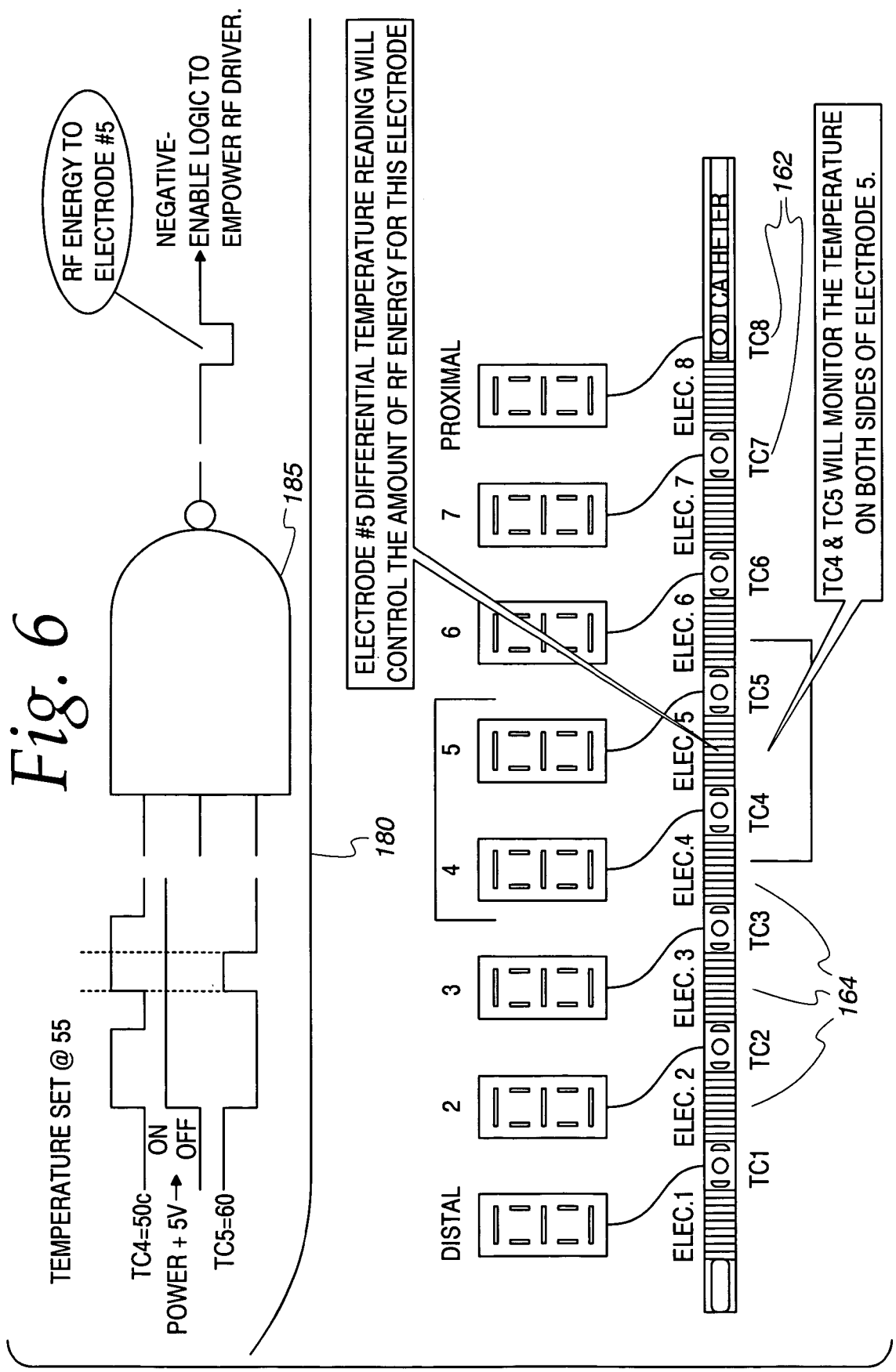
FIG. 6 shows a schematic diagram of temperature regulation circuitry used to regulate RF energy based on temperature readings according to the present invention.

The temperature regulation circuitry of this specific example is shown in more detail in FIG. 6. As mentioned above, each electrode 164 has a corresponding thermocouple sensor 162 that provides temperature feedback information at the tissue site immediately proximal to the electrode delivering the RF energy. Each electrode's RF output is controlled by a PWM circuit 180 located on each channel card. Temperature input signals sensed from neighboring thermocouples that are electronically subtracted from each other to form a new pulse width that will control the amount of RF energy output. For example, FIG. 6 illustrates the monitoring of both sides of electrode # 5 and the resulting differential PWM that will control the RF circuitry for this electrode. As illustrated, digital logic, herein NAND gate 185 is employed with inputs set by temperature thresholds taken from thermocouples adjacent to the electrodes.

Safety features that isolate the external RF generator (coupling transformers) from the power source are implemented both on the channel card as well as common electronics card.

The voltage, current, impedance, and output power are calculated by the analog computer unit (ACU) and the associated high precision RMS to DC converter circuitry. The information generated by the ACU is crucial to the precise control and stability of the system. This provides real-time monitoring of the catheter's parameters and stabilizes the preset temperature for a constant stream of energy in order to create a clean and accurate lesion.

As shown diagrammatically in FIGS. 5A-B, this interface provides an impedance and delta impedance cutoff for each channel individually. This will cause the power delivery to be interrupted from a given electrode when that electrode's impedance rises above a preset limit.

Over temperature, open thermocouple, high impedance, and high delta impedance detection circuitry are implemented into the design of the preferred example of an information processor and RF output controller (i.e. the IntelliTemp system) described herein. System shutdown occurs for over temperature detection on any channel Open thermocouple will inhibit operation on the affected channel only, normal operation proceeds on remaining channels.

The following parameters are used for real time analog computation of voltage impedance and power according to the specific example of an information processor and RF output controller described above:

Input Parameters:
Sensed AC Voltage, $V_{in}$, via secondary side of the input transformer.
Sensed AC Current, $I_{in}$, mA, via precision non-inductive resistor and associated circuitry.

Output Parameters:
Computed RMS Voltage, $V_{out}$, 100 mV/RMS representing 1 Volt, V.
Converted RMS Current, $I_{out}$, 10 mV/RMS representing 1 milliampere, mA.
Computed Impedance, $Z_{out}$, 1 mV/RMS representing 1 ohm, Ω.
Computed RMS Power, $P_{out}$, 100 mV/RMS representing 1 Watt, W.

The specific example of the information processor and RF output controller illustrated in FIGS. 3-7 does not rely on digital circuitry (e.g., analog-to-digital (A/D) converters, digital latches, registers, and a microprocessor) to determine sensed voltage, impedance, and power. Instead, it utilizes analog methods to provide real-time computation of RMS output, voltage, current, impedance and power.

Figure 5C:
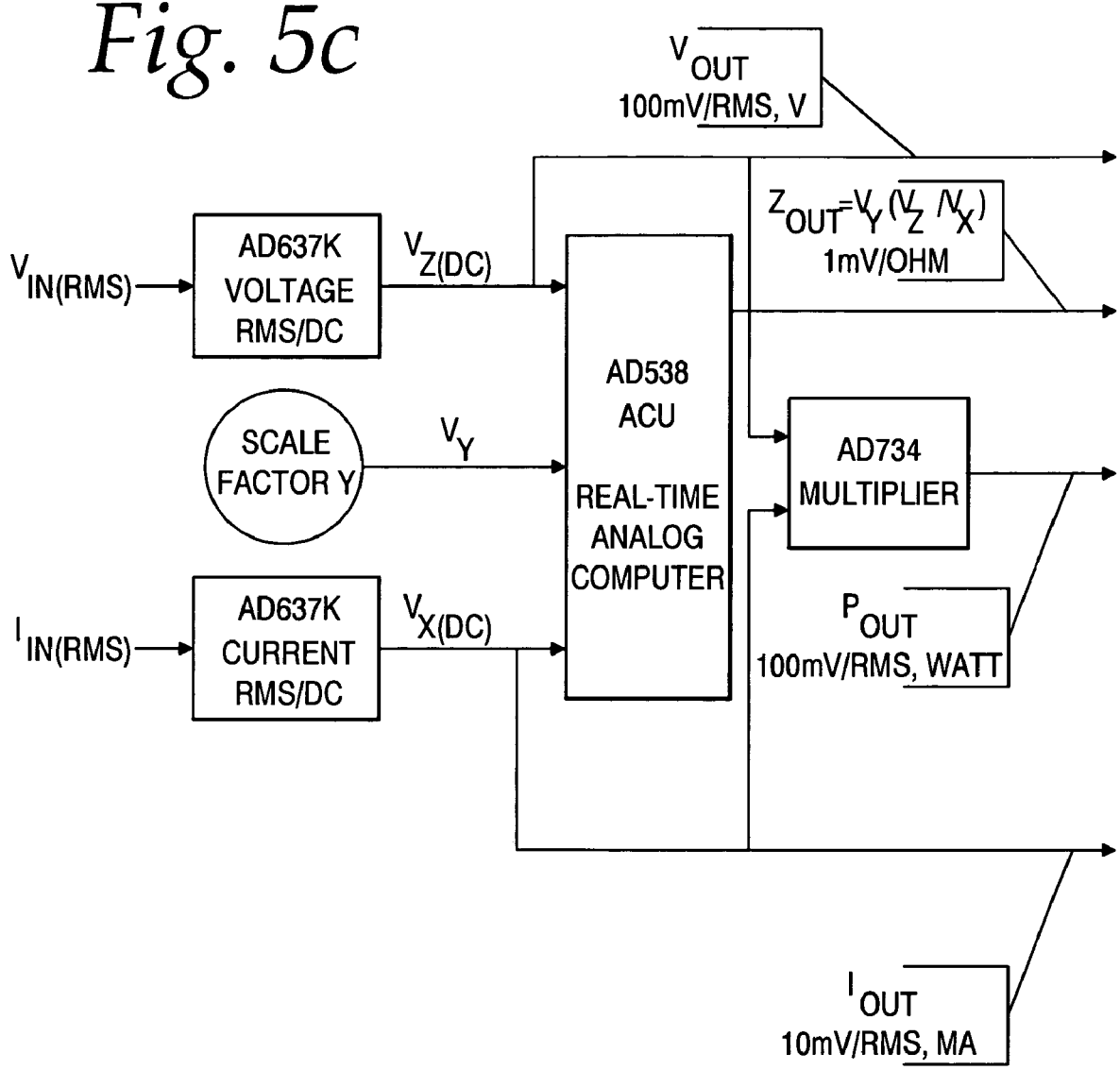
FIG. 5C is a block diagram illustrating real time analog computation of voltage impedance and power according to the present invention.

The building blocks for the real-time analog computer are illustrated in FIG. 5C and described below. It will be understood that this component is a computational module and, in other approaches, maybe based upon other types of components such as digital circuitry.

The primary building block for this analog computation circuitry is the Analog Devices AD538 Real-Time Analog Computation Unit (ACU) which provides precision analog multiplication, division, and exponentiation. The first two mathematical operations are used, as follows:

The ACU has this transfer function:

$$V_{OUT,ACU} = V_y(V_z/V_x)$$

It should be noted that this $V_{OUT,ACU}$ is not the overall $V_{OUT}$ of the analog computation system; it is merely the output of the AD538 device used. $V_z$ is a DC value that is an output parameter from the second set of building blocks mentioned below, the RMS-to-DC Converter. This DC value represents the RMS voltage (V) of the RF energy being delivered at the electrode. Similarly, $V_x$ is a DC value which has been converted from the RMS current (mA), of the RF energy being delivered at the electrode. This device also permits a scaling factor, $V_y$, to be multiplied into the output transfer function. This scaling factor is set at a value of 0.1, since the ratio of the primary to secondary coils of the input transformer is 10. Since $V_z$ represents voltage, and $V_x$ represents current, therefore $V_{OUT,ACU}$ represents the computed real-time impedance Ω.

The secondary building blocks are two Analog Devices AD637 High Precision Wide-Band RMS-to-DC Converters, which serve to compute the true RMS value of an incoming AC waveform, and represent this RMS value as an equivalent DC output voltage. The outputs of these units are fed as input parameters into the ACU discussed above, which also supplies a true RMS value of a signal that may be more useful than an average rectified signal since it relates directly to the power of the input signal.

The final building block is the Analog Device AD734 4-Quadrant Multiplier/Divider, which serves to multiply the DC value representing RMS Voltage, with the DC value representing RMS Current, to supply the product of these two terms, which is equivalent to Output Power, since $P_{out} = V_{out}I_{out}$ (W, Watts).

The outputs of $V_{out}$, $I_{out}$, $Z_{out}$, and $P_{out}$, are hence all calculated in real-time.

RF output per channel is governed by three inputs into a NAND gate (e.g., Motorola part number MC74HC10A):
 i. The "on time" of the pulse-width modulator for that particular channel.
 ii. The "on time" of the pulse-width modulator for the channel immediately proximal to the above-said channel.

iii. Power Limit Set-Point that is common for all channels. This is manually set with a control knob on the instrumentation front panel.

Figure 7:
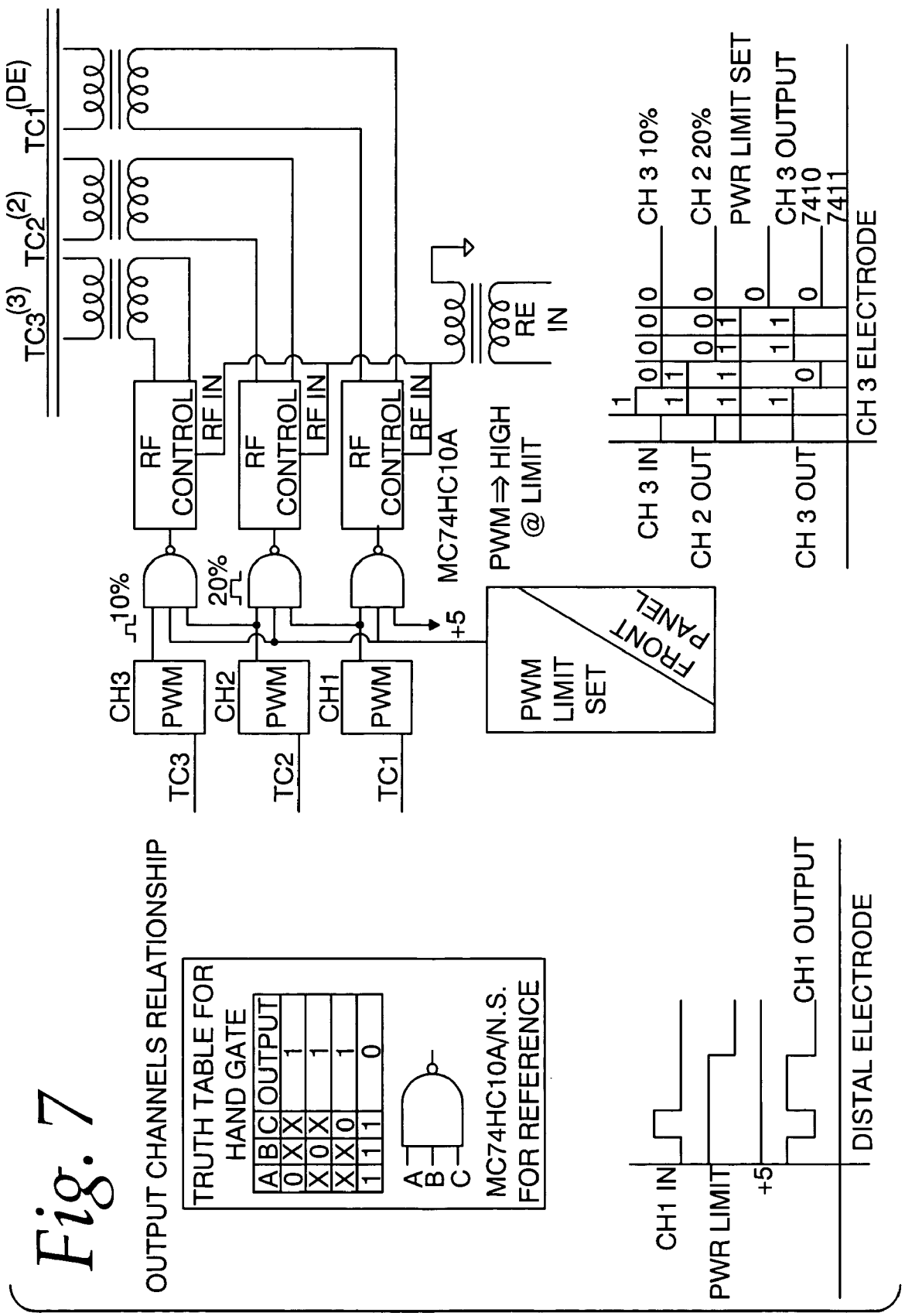
FIG. 7 is a block diagram showing the regulation of delivery of RF energy by an information processor and RF output controller according to one embodiment of the current invention that regulates current delivered to each ablation electrode of a series of ablation electrodes, separately using digital logic according to the present invention.

As an example, the functional schematic of the interaction between Channel 3 input and Channel 2 output in determining Channel 3 output is shown in FIG. 7, where in the timing diagram of the Channel 3 electrode output (lower right corner) there is a slight propagation delay.

The PWM duty cycle is governed by an oscillator that is set by an oscillating frequency determined by a resistive and a capacitive component. In the present embodiment, this frequency is set at 1.7 kHz. However, if the sensitivity of the feedback-response circuit needs to be "slowed down" to increase heat build-up in the tissue, this frequency can be decreased.

Figure 8:
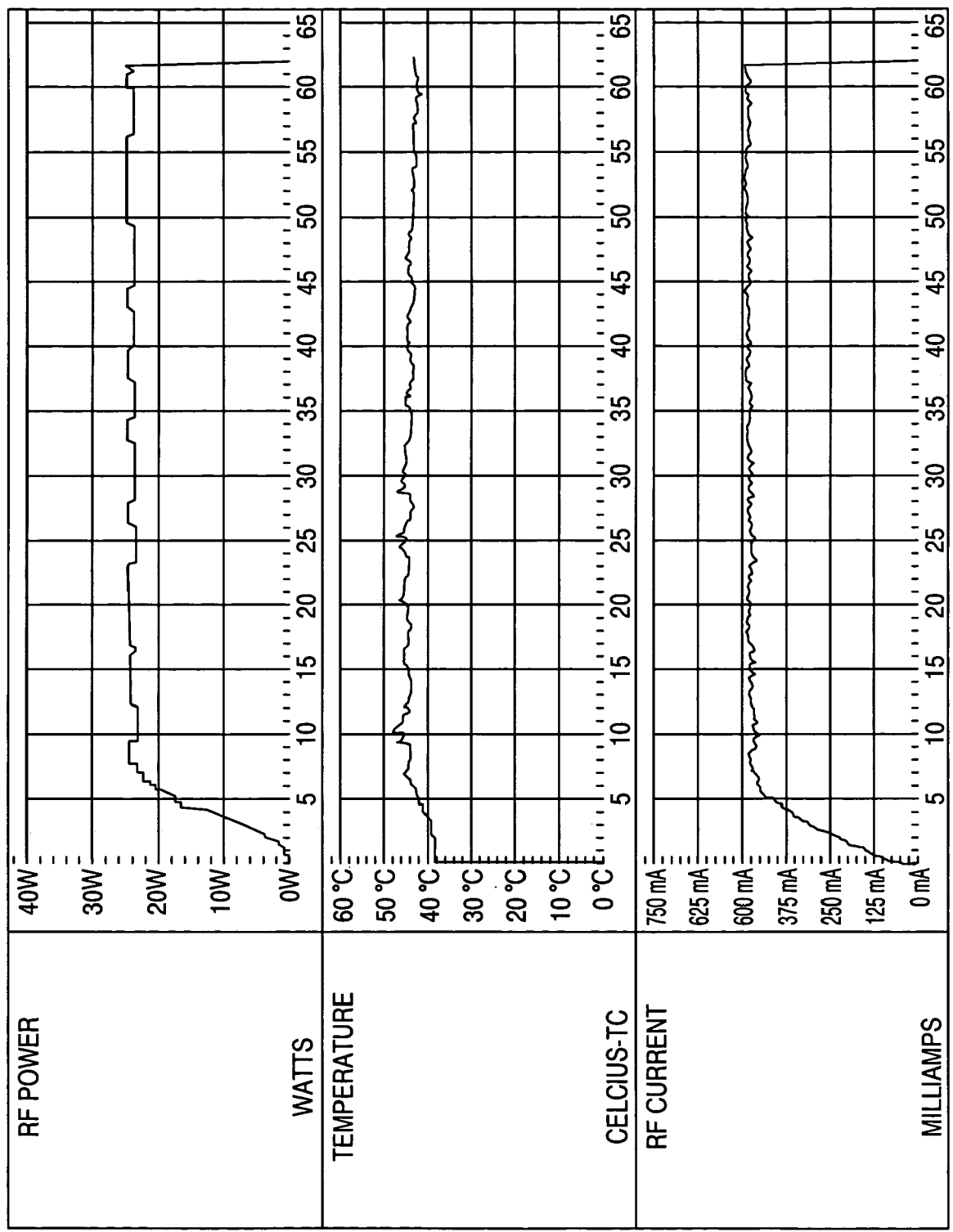
FIG. 8 shows a record of a typical ablation episode using the methods and procedures of the current invention according to the present invention.

FIG. 8 shows a typical ablation episode using the specific embodiment of the invention described above. Contact force is a parameter that has been measured experimentally in an in vitro setting to determine the quality of electrode-tissue contact; it has a high correlation (up to 97%) with temperature rise. Thus, when there is excellent electrode-tissue contact, there is a regular flow of RF energy transmitted into the tissue that is converted into heat energy. When this condition exists, the monitored tissue impedance and voltage is relatively constant. Therefore, the measured tissue impedance is another key parameter, because it is an indicator of electrode-tissue contact.

As described above, the information processor and RF output controller of the current invention, as well as the systems and methods of the current invention, are designed to maximize the efficacy of an ablation procedure by minimizing coagulum formation. Not to be limited by theory, these information processor and RF output controllers, systems, and methods take advantage of the following considerations. When tissue contact is good and stable, the impedance is relatively low and constant. As a result, less RF energy is required to reach the desired set temperature, with a shorter "ramp up" time and a lower wattage required to maintain the set temperature. The risk of coagulum formation is low because RF energy is effectively transmitted into the tissue, and heat is generated within the tissue rather than at the blood layer.

Conversely, when electrode-tissue contact is intermittent, the impedance value fluctuates and the power delivered also has to adapt rapidly in order to reach or maintain set temperature. This fluctuating waveform may be conducive for coagulum formation because the rapid back and forth switching between high and low impedance causes the output power waveform to approximates the coagulation waveform used in electrosurgery.

When electrode-tissue contact is marginal or poor, impedance can rise rapidly thereby requiring more RF energy to be delivered in a fast response to achieve the same set temperature. In this last scenario, because of poor electrode-tissue contact, there is a high probability that RF energy is lost into the blood layer surrounding the electrode, thus heating the blood rather than tissue and fostering coagulum formation. As coagulum forms on the electrode, impedance rises even more, hence bringing about a vicious cycle of climbing watts and escalating thrombus formation. Hence, one has to terminate the power delivery immediately when there is a sudden impedance rise, and the catheter should be withdrawn at this point to clean coagulum off the electrodes.

The following example describes and illustrates the methods, systems, and devices of the invention. The example is intended to be merely illustrative of the present invention, and not limiting thereof in either scope or spirit. Unless indicated otherwise, all percentages and ratios are by weight. Those skilled in the art will readily understand that variations of the materials, conditions, and processes described in these examples can be used. All references cited herein are incorporated by reference.

In one example, a study was performed to analyze factors that affect coagulation formation during cardiac ablation, and to set parameters to minimize coagulation formation during this procedure. More specifically, the study was performed, at least in part, to analyze the rate of RF power delivery through ablation catheter electrodes with respect to target temperature set-points, and to determine its correspondence to coagulum formation.

This study was based on RF ablation data from 398 independent ablation episodes derived from 15 patient cases randomly picked from Phase II of the CARDIMA REVELATION™ Tx U.S. multicenter clinical trials. Patient entry criteria were symptomatic paroxysmal atrial fibrillation (PAF), refractory to at least 2 anti-arrhythmic drugs, with 3 PAF episodes within the 30 day baseline observation period. In this multicenter clinical protocol, the use of anti-coagulation agents followed these guidelines for all patients receiving RF ablation: Coumadin OK was discontinued three (3) days prior to the procedure and low molecular weight heparin was administered the day preceding the procedure. At the time of the procedure, the international normalization ratio (INR) was checked to be <1.8, and a baseline activated clotting time (ACT) value was obtained. An initial bolus of intravenous heparin was administered, and continuously administered throughout the procedure to maintain an ACT of approximately 200 to 300 seconds. The ACT measurements were taken at 30 minute intervals until therapeutic levels were achieved, then every 60 minutes for the duration of the procedure. Heparin administration was adjusted according to the ACT values.

RF ablation procedures were performed using the REVELATION Tx (CARDIMA, Fremont, Calif., U.S.A.) Microcatheter. This microcatheter has eight 6 mm coil electrodes with 2 mm spacing, and eight inter-electrode thermocouples. A 9 Fr CARDIMA NAVIPORT™ steerable guiding catheter was used in conjunction with the microcatheter to aid in placement. If the target temperature was not reached, the duration to reach the mammal recorded temperature closest to the target temperature was used instead. The RFG-3E RF generator (Radionics, Burlington, Mass., U.S.A.) was the RF source used for all procedures.

Software running on a computer connected to this generator was used to record the time for attaining a pre-determined target temperature, as well as the RF power and current at that time, for each RF energy application. Measurements taken included the duration time (seconds), for attaining a pre-determined temperature set-point (i.e., 50° or 55° C.), and the power (watts) at that time. This was carried out for each RF energy delivery episode corresponding to each electrode. If the set-temperature was not reached, the duration to reach the maximal recorded temperature closest to the set-temperature was used instead. After each linear ablation trajectory, the catheter was withdrawn from the steerable guiding sheath, and each electrode was visually inspected. The presence or absence of coagulum was noted on clinical data sheets, thereby providing a record for analysis with the RF delivery parameters, (i.e. power, current, and duration to reach target temperature) that were logged automatically by software.

Based on the study described above, a mathematical model was used to calculate a value, the Coagulum Index, that provides insight into the likelihood of coagulum formation during an ablation procedure, and that is useful in setting parameters for an ablation procedure to minimize the potential for coagulum formation. From this model, Coagulum Index was defined:

$$\text{Coagulum Index} = (W/t)/I^2$$

Power=W (watts)

Current=I (amperes)

Duration to reach Set Temperature=t (seconds)

The term on the right-hand-side of the equation, (W/t), is the slope or gradient of the power curve measured from the start of the ablation episode (baseline) to the time that the target temperature (i.e. set point temperature) or maximum temperature is first reached in an ablation episode. The derivation of the Coagulum Index, which has no physical units, may be accomplished as follows.

A mathematical model for distinguishing between coagulum or non-coagulum formation on the RF-ablating electrode of the Cardima REVELATION Tx catheter was developed. This model was based on dimensional analysis of physical constants pertaining to the units for various logged parameters during RF ablation episodes, and was verified using clinical data obtained as described in the Example section.

Definitions in S. I. (System International) Units:

Mass=Kg[kilogram]

Length=m[meter]

Time=s[seconds]

Power=W[watts]=$Kg*m^2*s^{-3}$

Each single-electrode catheter ablation event has its own slope calculated from a plot of Power (Y-axis) vs. Time (X-axis), from baseline temperature (i.e., temperature of free-flowing blood in the heart=approximately 37° C.) to 50° C. In this analysis, this is the duration for the sensed temperature from a thermocouple to reach a set temperature, e.g., 50° C. If the set temperature cannot be reached, then it is the duration for the sensed temperature to reach the maximum temperature, for that ablation episode.

$$\text{Slope} = \text{Power}/\text{Time} \quad \text{(Equation 1)}$$
$$= (\text{Work Done}/\text{Time})/\text{Time}$$
$$= (\text{Force} * \text{Displacement})/\text{Time}^2$$
$$= (\text{Mass} * \text{acceleration} * \text{Displacement})/\text{Time}^2$$

Dimensional Analysis of the units show that:

$$\text{Slope} = Kg*m*s^{-2}*m/s^2 \quad \text{(Equation 2)}$$
$$= Kg*m^2*s^{-4}$$

It follows that 1/Slope is the reciprocal of (Equation 2):

$$1/\text{Slope} = Kg^{-1}*m^{-2}*s^4 \quad \text{(Equation 3)}$$

Now we define electrical capacitance, C, in terms of its fundamental units:

$$C = m^{-2}*Kg^{-1}*s^4*I^2 \text{[NIST]}$$

Rearranging terms, $C = Kg^{-1}*m^{-2}*s^4*I^2$ (Equation 4)

Dividing both sides by $I^2$:

$$C/I^2 = Kg^{-1}*m^{-2}*s^4 = t/W \quad \text{(Equation 5)}$$

Notice that (Equation 3)=(Equation 5)

Therefore, we can define capacitance as a function of the slope that we obtain for each ablation episode:

$$C = I^2*(t/W) = I^2(W/t) = I^2/\text{Slope} \quad \text{(Equation 6)}$$

In the presence of an alternating current, impedance Z is defined as:

$$Z = 1/(2\pi f C) \quad \text{(Equation 7)}$$

where f=operational RF frequency

Substituting (Equation 6) into (Equation 6), we are able to define Coagulum Index as follows:

$$\text{Relative Impedance} = k*(W/t)/I^2 \quad \text{(Equation 8)}$$

where $k=1/(2\pi f)$, and is constant for a particular RF generator, assuming that the RF oscillator frequency, f, is stable and constant. Therefore, for practical purposes, the proportionality constant k is ignored in the calculation since the same type of RF generator, the Radionics RFG-3E, was used throughout the study described in the Examples section. The results discussed in the Examples section showed a close correspondence between this calculated value and the probability of coagulum formation at the ablation electrode site. Therefore, the term Coagulum Index was given to this quantity and Coagulum Index=$(W/t)/I^2$.

Many dose-response relationships have been found to follow a logistic sigmoidal curve. Hence, the estimated probability of coagulum occurring, P(coag), is modeled statistically by a logistic model described by Equation 1 below, where the logit risk of coagulum is the dependant variable and the coagulum index (C.I.) is the independent or predictive variable.

$$P(coag) = \frac{e^{\alpha+\beta(C.I.)}}{1+e^{\alpha+\beta(C.I.)}} \quad \text{Equation 1}$$

$$\alpha = -5.2932$$

$$\beta = 0.3803$$

Figure 9:
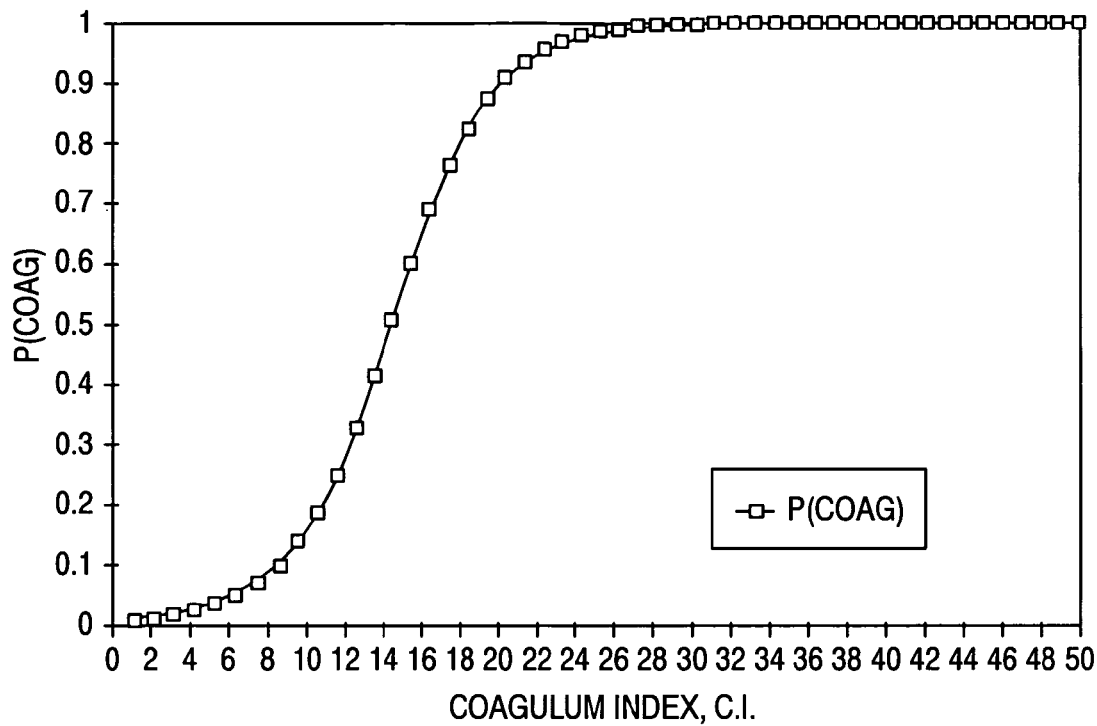
FIG. 9 is a graph of logistic function with estimated probability of coagulum as the Dependent Variable, and C.I. as the Predictor Variable.

FIG. 9 shows the graph of this logistic model. With this model, a threshold value for coagulum index (C.I.) can be found to indicate a high probability of coagulum occurring.

In a series of 398 ablation episodes from a total of 15 patient studies in the clinical studies described in this Example, it was found that the logistic model of risk of coagulum demonstrated a significant fit between Coagulum Index and the estimated percentage probability of coagulum occurring (p<0.001). Table I summarizes the finding that the estimated probability of coagulum formation increases significantly when Coagulun Index increases. This analysis revealed a clear correspondence between Coagulum Index and coagulum formation. Furthermore, a distinct threshold of Coagulum Index greater than or equal to 12 was established, beyond which coagulum formation is expected. Results of this study showed that coagulum could be reduced if the slope (W/t) was gentle. This was accomplished by gradually increasing the power delivered from the RF generator, as opposed to "cranking up the watts" at the very start of an ablation episode.

TABLE I

| C.I. | 4 | 8 | 12 | 16 | 20 | 24 |
|---|---|---|---|---|---|---|
| P(coag) % | 2 | 10 | 32 | 69 | 91 | 98 |

Figure 10A:
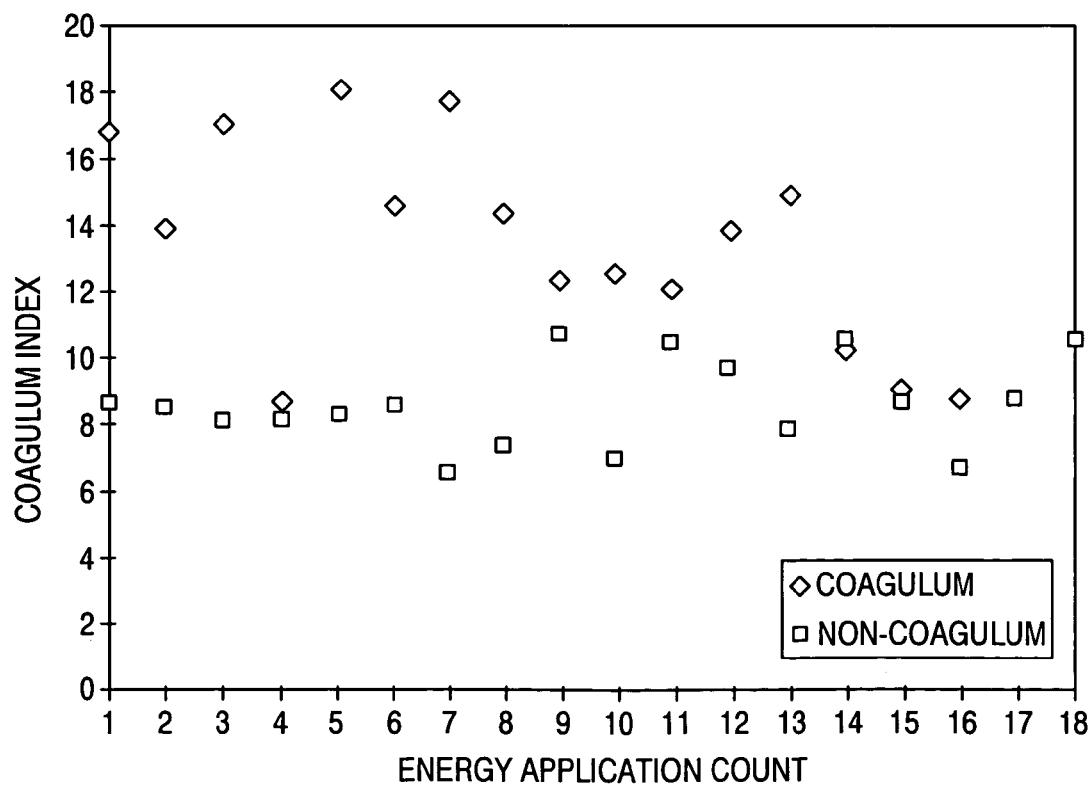
FIGS. 10A and 10B show representative scattergrams of coagulum index values from two RF ablation patient cases according to the present invention.
Figure 10B:
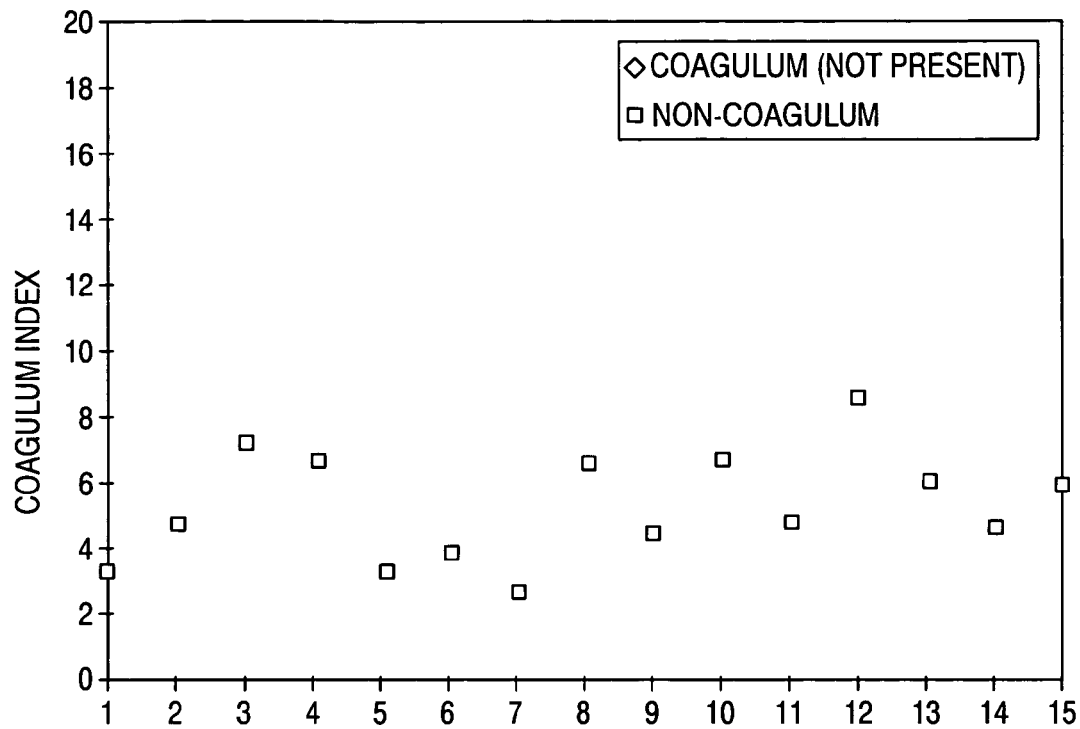

FIGS. 10A and 10B show representative scattergrams of Coagulum Index values from two RF ablation patient cases. This data supports the conclusion that the derived Coagulum Index value has pertinence and value in suggesting coagulum formation. The example depicted in FIG. 10B, with Coagulum Index values less than 12, showed no coagulum formation. On the other hand, coagulum was observed in many of the energy applications of FIG. 10A, especially for those having a Coagulum Index greater than 12. For the energy applications in FIG. 10B, lower Coagulum Indexes were obtained by gradually increasing power, in contrast to an immediate increase in power levels which was used for the energy applications shown FIG. 10A. Furthermore, the maximum power setting was reduced from 50 to 30 watts in FIG. 10B.

The clinical effectiveness was analyzed for linear ablation procedures where coagulation formation was absent. During Phase I, power delivery was not controlled in a gradual manner for each ablation episode and maximum power was set at 50 W. During Phase II, ablation was performed using a gradual power delivery (as described below) and maximum power was kept below 35 W. As summarized in Table II, after 6 months AF episodes were reduced in Phase II patient populations. In fact, the number of patients experiencing a greater than 50% reduction in AF episodes almost doubled when using the gradual power delivery and lower maximum power for each ablation episode. A significant increase was also observed in the number of patients that no longer had any AF episodes (100% reduction), from 30% in Phase I to 53% in Phase II.

TABLE II

| % Reduction of AF Episodes after 6 months | Phase I (N = 10) | Phase II (N = 17) |
|---|---|---|
| >50% reduction | 4/10 Patients (40%) | 13/17 patients (77%) |
| 100% reduction (no AF Episodes) | 3/10 Patients (30%) | 9/17 patients (53%) |

Thus, it appears that one mechanism for mitigating coagulum formation is to deliver RF power in such a way that the rise time of the power, and hence temperature curve, is more gradual and consistent. For example, when using the Radionics RFG-3E generator, with a set maximum of 30 watts, one should commence with a lower power setting of 10 watts for the about first 10 seconds, and then gradually adjust the knob on the RF generator to the set maximum of 30 watts, while still maintaining total RF delivery time at 60 seconds. When this technique was applied, it decreased coagulum formation, as is evident by the data shown in FIG. 10.

Specific characteristics of RF generators must be considered to obtain the gradual power rise described above. The IBI-1500T has 4 user-selectable choices for controlling the power delivery ramp-up curve. The Osypka 300 Smart and Cordis Webster Stockert have built-in algorithms which appear to automatically regulate power delivery rise time in a gradual manner, the latter allowing the end-user to specify a temperature ramp-up time. And finally, the Medtronic Atakr has no user override controls for power delivery application. In comparison, the Radionics RFG-3E allows the user to manually increase power output during the delivery of RF energy. In the present embodiment of this invention, the output power setting for RF energy to be delivered at the electrodes are user adjustable via the front panel knob (1-30 Watt). A lower power setting will increase the ramping time, since it takes a longer time to reach set temperature. An automatic algorithm which calculates the coagulum index (C.I.) in real-time can be incorporated into the information processor and RF output controller functionality so that a visual or auditory signal can alert the end-user whenever the risk for coagulum formation is high, i.e. C.I. greater or equal to 12. Alternatively, the information processor and calculate the C.I. in real-time and use this calculated value as information that is fed back to the RF output controller functionality so that the ablation episode can be carried out with minimal probability of coagulum formation.

Excellent electrode-tissue contact is determined by a combination of fluoroscopy, low initial impedance, and the quality of electrograms during the procedure. Results from the study reveal that excellent electrode-tissue contact, in combination with gradual RF power delivery to a maximum level of 30 to 35 watts, constitutes a sound prescription for best practice of RF ablation with the least likelihood of coagulum formation at the electrode site. Bench testing of tissue ablation has also demonstrated that good electrode contact with the tissue results in lower RF power consumption required to reach set temperature. Lower RF energy requirements in turn reduce the probability of coagulum formation.

The insights revealed in this example may be extrapolated to procedures using other catheters for other RF ablation procedures as well, and hence are presented here. The catheter MAZE procedure calls for the creation of linear 'barricades' along anatomical trajectories within the right atrium, using RF ablation to compartmentalize the chamber and 'contain' pro-arrhythmic electrical propagation.

Results of this study reveal the following considerations regarding minimizing coagulum formation during cardiac tissue ablation. In ideal situations, it is possible to achieve satisfactory tissue contact for all eight linear ablation catheter electrodes. However, the techniques discussed below yield acceptable results in right atrial MAZE linear ablation procedures even when the anatomical or flow conditions prevent optimal simultaneous contact of eight catheter electrodes.

a) Excellent contact should be established in as many linear array electrodes as possible.
b) Low tissue impedance at 'baseline' is indicative of effective contact; some RF generators permit this to be sensed and displayed prior to actual ablation by emitting a small RF current to interrogate tissue impedance at the ablation site.
c) Pacing threshold, if used as an indicator of contact, should be reasonable (1-2 mA); threshold values above 4-5 mA most likely indicate poor contact, and the catheter should be repositioned.
d) The sheath should be rinsed periodically (e.g. every 15 minutes) with a standard heparinized saline solution bolus. This improves contact by removing coagulum build-up on the electrodes and catheter shaft. If possible, the catheter should be pulled out of the Naviport deflectable guiding sheath after each trajectory, the electrodes should be wiped clean if needed, before re-introducing the catheter into the Naviport.

In addition to achieving excellent electrode-tissue contact, reduced coagulum formation can be obtained by regulating the RF power settings such that power is gradually increased and by setting the generator maximum power settings to 30 W-35 W with power monitored continuously. The catheter should be repositioned as needed to maintain set temperature at a lower power level. It has been observed that coagulum formation is more evident when power required to maintain set temperature approaches 50 W. Conversely, coagulum formation is minimized greatly when power required is less than 35 W. This may be seen as a challenge when trying to reach set temperature. However, with excellent electrode-tissue contact, desired set temperature can be achieved with as low as 7 W to 15 W of power delivery. In vivo animal studies have verified deep, transmural lesions with these low power settings when there is sufficient electrode-tissue contact.

Figure 11:
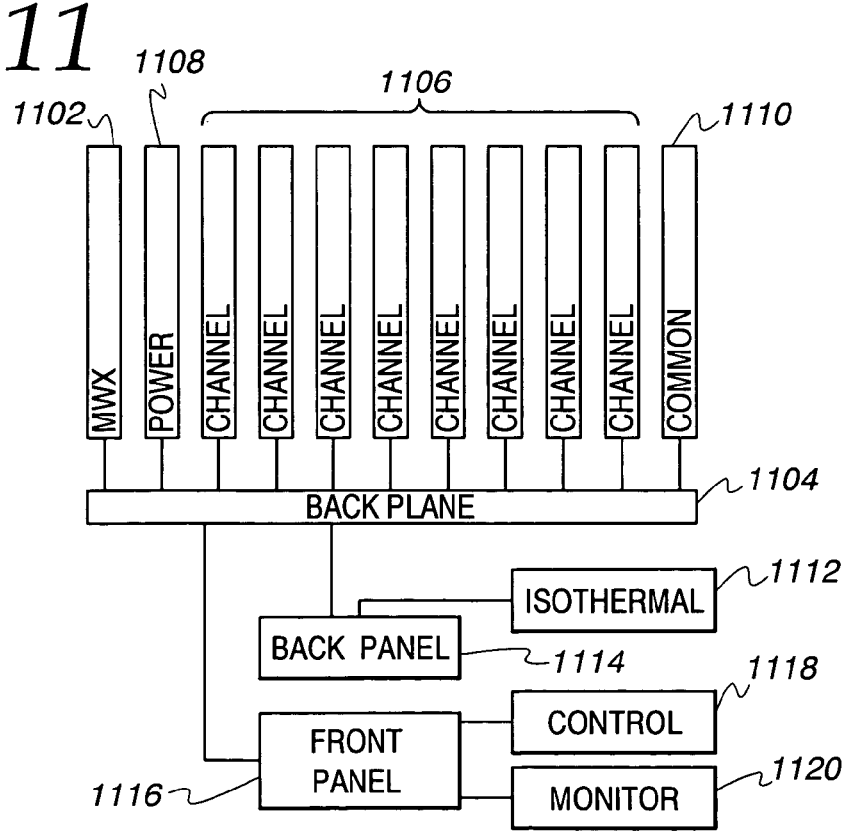
FIG. 11 is a functional block diagram of a system for delivering RF energy to a catheter according to the present invention.
Figure 12B:
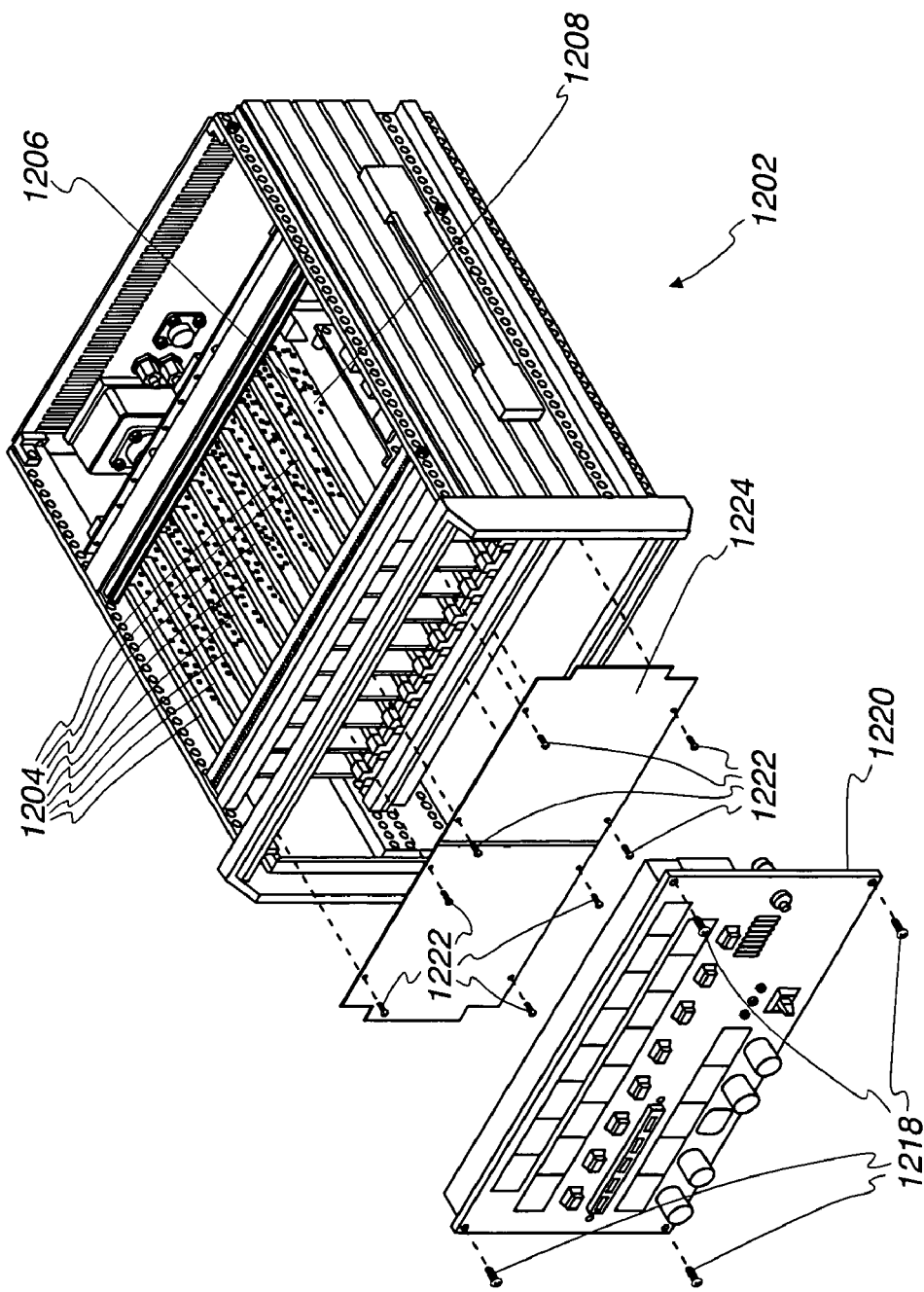
Figure 12C:
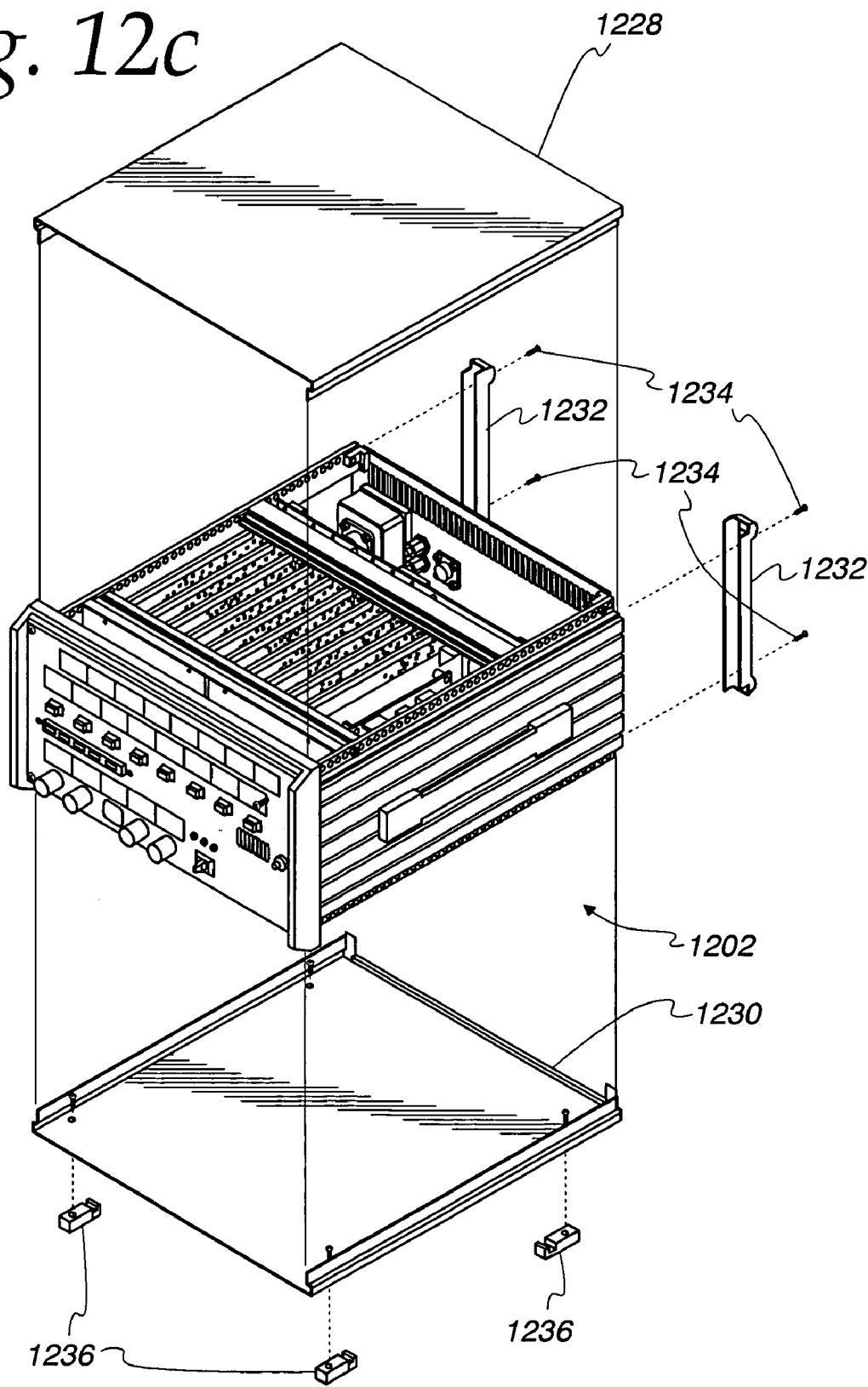
Figure 12D:
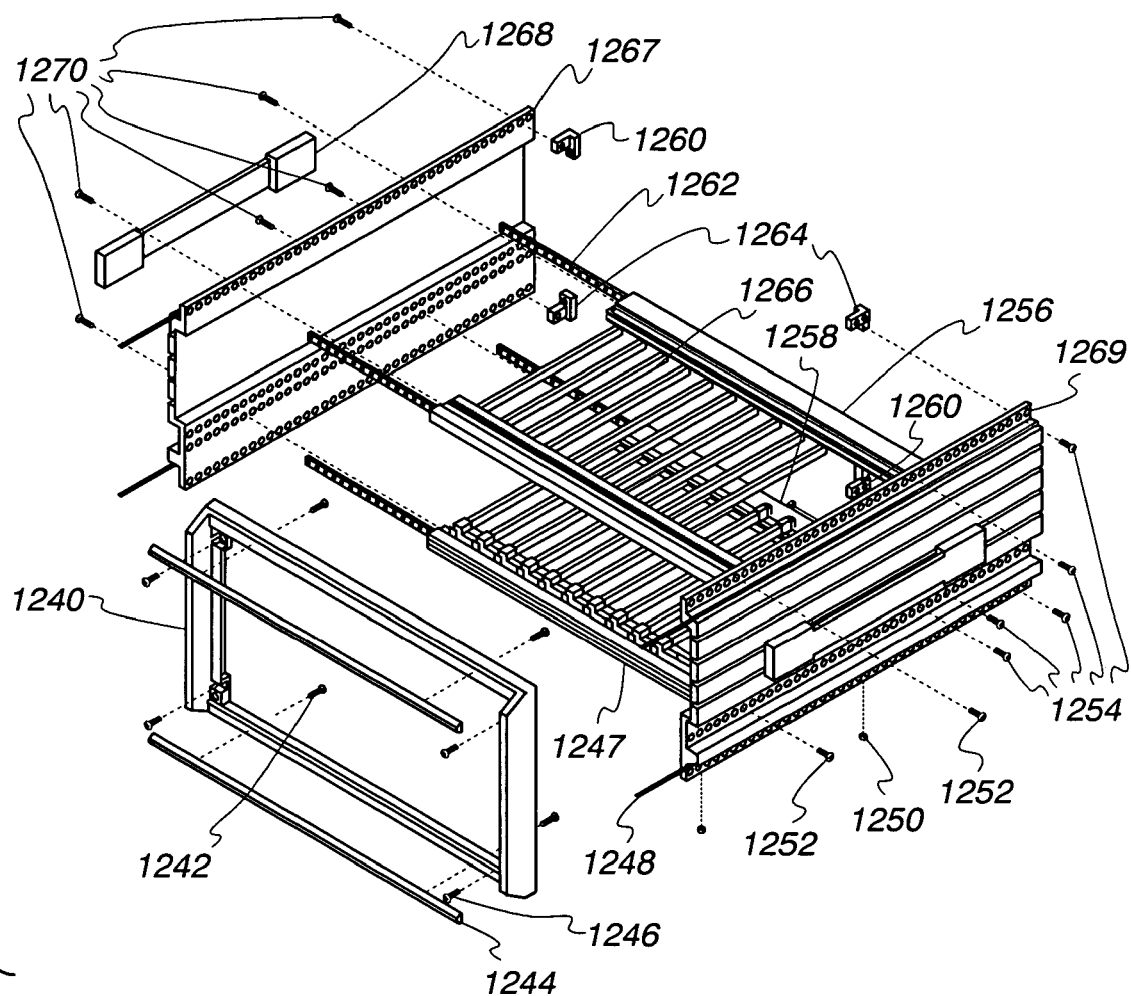
Figure 12E:
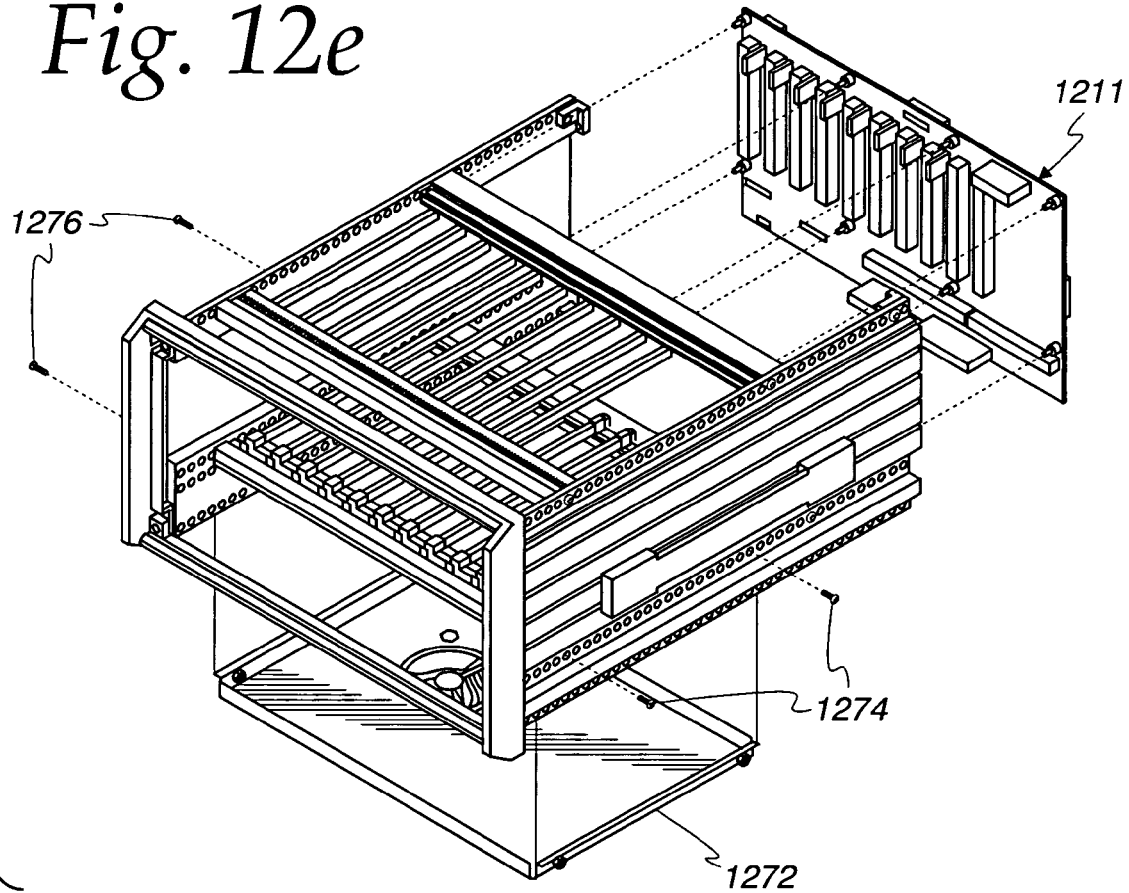
Figure 12F:
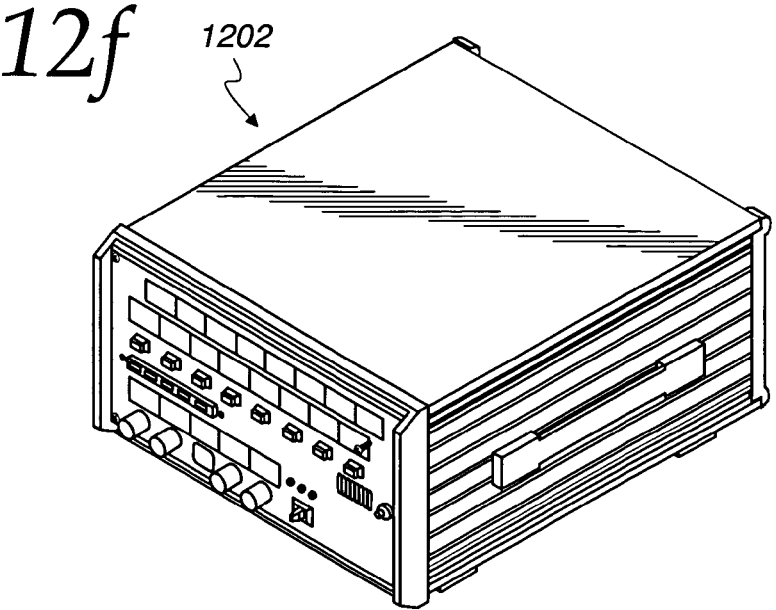

Referring now to FIG. 11, an example of a system 1102 for the ablation of tissue using RF energy is described. A backplane 1104 is connected to eight modular RF channel cards 1106. The backplane 1104 conducts RF energy and communications between the cards. Although eight channel cards 1106 are shown, it will be understood that any number of channel cards may be used.

Each of the channel cards 1106 supply RF energy to a particular channel as described elsewhere in this specification. In other words, the channel cards each use substantially only analog means to compute the amount and timing of the RF energy applied to the electrode. Also as described elsewhere in this specification, the channel cards 1106 receive feedback signals, for instance, signals indicating temperature to the channel cards 1106. However, in another approach, the system may be based upon other technology, for instance, digital components or neural networks.

The channel cards 1106 easily plug and to and may be removed from the backplane 1104. In this regard, the backplane card 1104 may include a socket corresponding to a connector on any of the channel cards 1106. A user simply pushes one of the channel cards into the corresponding sockets on a backplane 1104 to make a connection Thus, attachment and removal of the card is easy and quick to accomplish.

The channel cards 1106 may include any number of analog components, which are organized into modules. For instance, one module may be the PWM module (with discrete components) and another may be the analog computer (with discrete components) as described previously in this specification. In other approaches, the system may be based upon other technology, for instance, digital components or neural networks.

A MUX card 1102 is also connected to the backplane 1104. The MUX card 1102 provides/switches analog and digital signals to a front panel 1116 and other components. The front panel 1116 is a user interface and also is connected to control unit 1118 and monitoring unit 1120. The control unit 1118 allows a user to control various system parameters and the monitoring component 1120 allows the user to monitor various system parameters as described elsewhere in this specification.

A power card 1108 provides power to other system components. A common electronics card 1110 provides common functions, for instance, timing information to system components. The isothermal box 1112 provides a connector to the catheter and includes a circuit for thermocouple cold junction compensation. This element controls the temperature of the junctions to thermocouple wires.

As has been described, control in the system is decentralized. In other words, no centralized control card or controller is responsible for system operation. Instead, control is distributed amongst the channel cards, which are modularly divided into discrete modules. Decisions concerning the timing and amount of RF energy to apply to the electrode element are made individually on each channel card. Thus, the cards themselves can be easily replaced and updated as can the modules on the cards.

Referring collectively to FIGS. 12a-f, a channel card assembly 1202 is described. The assembly 1202 comprises channel cards 1204. The channel cards 1204 have been described elsewhere in this specification and, in one approach, includes an RF output controller and information processor. The channel cards 1204 include analog components for determining the amount of timing of RF energy applied to ablation catheter (not shown).

The channel cards 1209 slide into channels 1209 for placement inside the assembly 1202. The channel cards 1204 provide proportional power control for a channel in order to provide smooth and stable temperature profiles with time. A pulse width modulator (PWM) is used to meter power proportionately to the catheter electronics. The PWM determines the RF power level delivered to an individual ablation electrode by varying the duty factor of the waveform, for instance, from zero to 99.5%.

The common analog electronics card 1206 receives RF energy from an external generator and couples the energy (via a transformer) to the channel cards 1204. The RF level is monitored and rectified to direct current (DC). The common electronics card 1206 also includes a master clock to synchronize the oscillators on the channel cars 1204 by providing pulses that are slightly faster than the free-running frequency of the oscillators on the channel cards. The common electronics card 1206 may provide other functions such as fault detection and provide relays.

The multiplexer card 1208 provides an analog and digital monitor signal to an external user interface. A power supply card 1210 includes power supply components to operate the cards 1205, 1206 and 1208. The cards 1204, 1206, 1208 and 1210 slide into slots 1209 of a backplane 1211. The backplane 1211 provides an electrical path between the cards 1204, 1206, 1208 and 1210. For instance, power supply card 1210 may supply power to the other cards 1204, 1206 and 1208 via the backplane 1211.

The front panel 1228 includes temperature meters from the individual channel cards. The front panel also includes parameter display meters driven by the multiplexers of the multiplexer card. For instance, power, voltage, and current may be displayed. Set points (set by turn potentiometers) to set parameters (e.g. temperature, temperature limit, power limit, impedance limit and delta impedance limit) and fault LEDs (e.g., for over temperature, open thermocouple, impedance, and delta impendence) may also be provided. The front panel 1220 is fitted onto the front of the assembly 1202 via screws 1218.

The back panel 1216 provides mounting for the card connectors, front panel connectors, back panel connectors and distribution lines for DC and RF sources. The back panel 1216 is fitted into the back of the assembly by screws 1214.

Blocking card panels 1224 fit under the front panel and is attached to the assembly. The front panel 1220 is a user interface to allow a user to enter values and control information as described elsewhere in this application.

The front panel 1228 and bottom panel 1230 are fitted to the bottom of the assembly 1202. Rear feet 1232 are attached to the assembly 1202 via screws 1234 to allow attachment of the assembly 1202 to other arrangements. Plastic feet 1236 allow the assembly to conveniently sit on a surface.

For carrying, a handle 1268 may be secured to the assembly by screws 70. A frame 1240 provides the front end support for the assembly and is secured by screws 1246. A top rail assembly 1256 holds guide rails 1266. This assemblage 1202 is supported by brackets 1260 and 1264 which are secured to sides 1267 and 1269. Bottom rail assembly 1247 holds rails and is secured by various screws. A decorative strip 1244 is secured to the assembly by screws 1246. Screws 1250, 1252, 1254 and 1274 and 1276 secured the rail assemblies 1256 and 1247 to the assembly.

While there has been illustrated and described a preferred embodiment of the present invention, it will be appreciated that modifications may occur to those skilled in the art, and it is intended in the appended claims to cover all those changes and modifications which fall within the true spirit and scope of the present invention.

What is claimed is:

1. A modular system including an external ablation device and a power source for delivering radio frequency (RF) energy from the power source to the external ablation device, the modular system comprising:
   a computational module for calculating RF power delivery parameters from at least one received measurement; and
   a pulse width modulator (PWM) module coupled to the computational module and to a single channel of the external ablation device, the PWM module forming and supplying an RF power output from the power source to the external ablation device, the magnitude and timing of the RF power output based at least in part upon at least one sensed temperature received by the PWM module from the external ablation device and the RF power delivery parameters.

2. The modular system of claim 1 wherein the computational module is substantially analog.

3. The modular system of claim 1 wherein the at least one sensed measurement comprises voltage and current measurements.

4. The modular system of claim 3 wherein the computational module is comprised of at least one analog chip for converting the voltage and current measurements into root mean squared (RMS) values and performing a selected mathematical operation on the RMS values.

5. The modular system of claim 1, wherein data computed by the computational module is used to determine an index indicative of the likelihood of coagulum.

6. The modular system of claim 1, wherein the external ablation device is chosen from a group comprising an ablation catheter and therapeutic probe.

7. A system for efficient delivery of radio frequency (RF) energy to cardiac tissue with an ablation device, the system comprising:
   a backplane; and
   at least one modular channel card removably coupled to the backplane for controlling the amount of RF power delivered through a single channel via an electrical coupling to at least one ablation electrode on the device.

8. The system of claim 7 further comprising an RF generator coupled to the at least one channel card.

9. The system of claim 7 further comprising at least one temperature sensor each positioned in proximity to the at least one ablation electrode, the at least one temperature sensor effective for measuring the temperature of the cardiac tissue in contact with the at least one ablation electrode.

10. The system of claim 7 wherein the electrical coupling is effective for delivering an electric current from an RF generator through the at least one ablation electrode, arranged in a linear or curvilinear assembly at a distal section of the device to the cardiac tissue and a return path of RF current through a reference electrode.

11. The system of claim 7 wherein the at least one channel card comprises an information processor module and RF output controller module.

12. The system of claim 11, further comprising a current sensor effective for measuring current delivered through said electrical coupling, and a voltage sensor effective for measuring voltage delivered through said electrical coupling, wherein the information processor and RF output controller are capable of calculating RF power and impedance in real-time and terminating delivery of RF energy through the electrical coupling based on changes in measured current and voltage, calculated impedance, and calculated power, and wherein the information processor and RF output controller provide RF energy simultaneously to all or any combination of the multiplicity of electrodes in a user-selectable manner.

13. A system as recited in claim 11, wherein said information processor and RF output controller compares the temperature measured at a series of temperature sensors to a user-selected target temperature for ablation of cardiac tissue, and wherein said information processor and RF output controller limits the delivery of the electrical current through said electrical coupling to maintain the target temperature at the cardiac tissue.

14. The method of claim 13, wherein each temperature sensor of the series of temperature sensors is adjacent to an electrode of the series of electrodes, and wherein the information processor and RF output controller utilizes a combined temperature reading from the temperature sensors on both sides of each electrode of the assembly of electrodes to independently control the delivery of current to each electrode.

15. A system as recited in claim 11, wherein said information processor and RF output controller compute the elapsed time for the temperature measured at said temperature sensor to ramp up to a target temperature, the measured ramp up to the target temperature being representative of the power curve indicating power transferred to cardiac tissue, said information processor and RF output controller calculating the slope of the power curve for an ablation event from the elapsed time and the target temperature for determining the likelihood of coagulum formation.

16. A system as recited in claim 15, wherein said information processor and RF output controller computes an index indicative of the likelihood of coagulum by dividing the slope of the power curve by the square of the electrical current delivered through the ablation electrode.

17. A system as recited in claim 11, wherein the system further comprises a multiplicity of current and voltage sensors and the information processor and RF output controller comprises functionality for terminating delivery of RF energy to the series of ablation electrodes by comparing to maximum set points, real-time measurements of at least one of impedance at the ablation site, differential impedance at the ablation site, and temperature at the ablation site.

18. The system as recited in claim 17, wherein the functionality utilizes analog methods for information processing and pulse width modulation for RF energy control.

19. A system as recited in claim 18, wherein said information processor and RF output controller computes a Coagulum Index associated with capacitive properties of the ablation of cardiac tissue at a selected radio frequency as proportional to the index indicating the likelihood of coagulum formation.

20. A system as recited in claim 19, wherein the Coagulum Index of the ablation device is provided for matching the impedance determined for the ablation of cardiac tissue.

21. A system as recited in claim 11, wherein delivery of electrical current is limited based on temperature measurements using analog methods for information processing and pulse width modulation for RF energy control.

22. The system of claim 7 wherein the at least one modular channel card comprises a first modular channel card and a second modular channel card and wherein the backplane conducts RF energy and communications between the first modular channel card and the second modular channel card.

23. The system of claim 7 wherein the channel card is substantially analog-based.

24. The system of claim 7 wherein the channel card is substantially non-analog-based.

25. The system of claim 24 wherein the channel card is substantially digital.

26. The system of claim 24 wherein the channel card includes neural networks.

27. A system for efficient delivery of radio frequency (RF) energy to cardiac tissue with an ablation device, said system comprising:
    an RF generator;
    a backplane;
    an electrical coupling effective for delivering an electrical current from the RF generator through a multiplicity of ablation electrodes, arranged in a linear or curvilinear assembly at the distal section of the ablation device, to the cardiac tissue and a return path for the RF current through a reference electrode;
    a multiplicity of temperature sensors each positioned in proximity to each of the multiplicity of ablation electrodes, said multiplicity of temperature sensors effective for measuring the temperature of cardiac tissue in contact with the multiplicity of ablation electrodes; and
    at least a single channel card, coupled to the backplane, the at least one channel card comprising an information processor and RF output controller effective for controlling the amount of RF power delivered through the electrical coupling.

* * * * *